US010370378B2

(12) United States Patent
Kemp et al.

(10) Patent No.: US 10,370,378 B2
(45) Date of Patent: Aug. 6, 2019

(54) TREATMENT OF SLEEP DISORDERS

(71) Applicant: Evotec International GmbH, Hamburg (DE)

(72) Inventors: John Alan Kemp, Basel (CH); Ian Michael Hunneyball, Abingdon (GB); Timothy Tasker, Isleworth (GB)

(73) Assignee: EVOTEC INTERNATIONAL GMBH, Hamburg (DE)

( * ) Notice: Subject to any disclaimer, the term of this patent is extended or adjusted under 35 U.S.C. 154(b) by 0 days.

(21) Appl. No.: 14/244,085

(22) Filed: Apr. 3, 2014

(65) Prior Publication Data

US 2014/0228562 A1    Aug. 14, 2014

Related U.S. Application Data

(63) Continuation of application No. 12/673,598, filed as application No. PCT/EP2008/006810 on Aug. 19, 2008, now abandoned.

(60) Provisional application No. 60/980,326, filed on Oct. 16, 2007.

(30) Foreign Application Priority Data

Aug. 20, 2007 (EP) .................................... 07114635

(51) Int. Cl.
*C07D 487/04* (2006.01)
*A61K 31/5517* (2006.01)

(52) U.S. Cl.
CPC ........ *C07D 487/04* (2013.01); *A61K 31/5517* (2013.01)

(58) Field of Classification Search
None
See application file for complete search history.

(56) References Cited

U.S. PATENT DOCUMENTS

| | | | |
|---|---|---|---|
| 4,316,839 A | 2/1982 | Gerecke et al. |
| 4,346,030 A | 8/1982 | Gerecke et al. |
| 4,346,031 A | 8/1982 | Gerecke et al. |
| 4,346,032 A | 8/1982 | Gerecke et al. |
| 4,346,033 A | 8/1982 | Gerecke et al. |
| 4,346,034 A | 8/1982 | Gerecke et al. |
| 4,346,035 A | 8/1982 | Gerecke et al. |
| 4,346,036 A | 8/1982 | Gerecke et al. |
| 4,352,815 A | 10/1982 | Hunkeler et al. |
| 4,352,816 A | 10/1982 | Hunkeler et al. |
| 4,352,817 A | 10/1982 | Hunkeler et al. |
| 4,352,818 A | 10/1982 | Hunkeler et al. |
| 4,353,827 A | 10/1982 | Hunkeler et al. |
| 4,359,420 A | 11/1982 | Gerecke et al. |
| 4,362,732 A | 12/1982 | Hunkeler et al. |
| 4,363,762 A | 12/1982 | Gerecke et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,489,003 A | 12/1984 | Hunkeler et al. |
| 4,507,313 A | 3/1985 | Braestrup et al. |
| 4,622,320 A | 11/1986 | Waetjen et al. |
| 4,622,321 A | 11/1986 | Waetjen et al. |
| 4,670,433 A | 6/1987 | Waetjen et al. |
| 4,727,153 A | 2/1988 | Waetjen et al. |
| 4,745,112 A | 5/1988 | Waetjen et al. |
| 4,771,051 A | 9/1988 | Waetjen et al. |
| 4,772,599 A | 9/1988 | Waetjen et al. |
| 4,772,696 A | 9/1988 | Waetjen et al. |
| 4,774,245 A | 9/1988 | Waetjen et al. |
| 4,775,671 A | 10/1988 | Hunkeler et al. |
| 4,780,539 A | 10/1988 | Waetjen et al. |
| 4,795,749 A | 1/1989 | Waetjen et al. |
| 4,870,073 A | 9/1989 | Waetjen et al. |
| 4,880,799 A | 11/1989 | Waetjen et al. |
| 4,886,797 A | 12/1989 | Waetjen et al. |
| 4,904,654 A | 2/1990 | Lin et al. |
| 4,939,139 A | 7/1990 | Lin et al. |
| 4,977,258 A | 12/1990 | Houghton et al. |
| 5,095,015 A * | 3/1992 | Albaugh .................. 514/212.06 |
| 5,665,718 A | 9/1997 | Godel et al. |
| 5,885,986 A | 3/1999 | Buettelmann et al. |
| 5,962,450 A | 10/1999 | Buettelmann et al. |
| 6,015,544 A | 1/2000 | Foged et al. |
| 6,174,881 B1 | 1/2001 | Borer et al. |
| 6,281,353 B1 | 8/2001 | Hoffmann-Emery |
| 6,391,873 B1 | 5/2002 | Jenck et al. |
| 2009/0054412 A1 | 2/2009 | Kemp et al. |

FOREIGN PATENT DOCUMENTS

| | | |
|---|---|---|
| CA | 2031898 A1 | 6/1991 |
| CA | 2372040 A | 11/2000 |
| CN | 1350538 A | 5/2002 |
| EP | 0 336 466 A1 | 10/1989 |
| EP | 0 672 666 A2 | 9/1995 |
| JP | 2002-544277 A | 12/2002 |
| SU | 1748647 A3 | 7/1992 |
| WO | 00/69858 A1 | 11/2000 |

OTHER PUBLICATIONS

M.C. Mauri et al., "Quazepam Versus Triazolam in Patients with Sleep Disorders: A Double-Blind Study," 13(3) Int. J. Clin. Pharmacol. Res. 173-177 (1993).
Abraham Sunshine, "Comparison of the Hypnotic Activity of Triazolam, Flurazepam Hydrochloride, and Placebo," 17 Clin. Pharmacol. Ther. 573-577 (1975).
Louis F. Fabre, Jr. et al., "Preference Studies of Triazolam with Standard Hypnotics in Out-Patients with Insomnia," 4 J. Int. Med. Res. 247-254 (1976).
P. Lomen et al., "Hypnotic Efficacy of Triazolam and Methyprylon in Insomniac In-Patients," 4 J. Int. Med. Res. 55-58 (1976).
Gerald W. Vogel et al., "A Comparison of the Effects of Flurazepam 30 mg and Triazolam 0.5 mg on the Sleep of Insomniacs," 47 Psychopharmacology (Berl) 81-86 (1976).

(Continued)

*Primary Examiner* — Sreenivasan Padmanabhan
*Assistant Examiner* — Jody L Karol
(74) *Attorney, Agent, or Firm* — Venable LLP

(57) ABSTRACT

The use of 7-chloro-3-(5-dimethylaminomethyl-[1,2,4]oxadiazol-3-yl)-5methyl-4,5-dihydro-imidazol[1,5,-a][1,4]benzodiazepine-6-one or its pharmaceutically acceptable salt for treating various types of insomnia.

18 Claims, 27 Drawing Sheets

(56) References Cited

OTHER PUBLICATIONS

Angela J. Bowen, "Comparative Efficacy of Triazolam, Flurazepam and Placebo in Out-Patients Insomniacs," 6 J. Int. Med. Res. 337-342 (1978).
K. Kay Okawa et al., "A Clinical Comparison of Triazolam with Placebo and with Secobarbital in Insomniac Patients," 6 J. Int. Med. Res. 343-347 (1978).
D.A.-C. Hegelbach-Feller et al., "Comparison of the short-acting benzodiazepines midazolam and triazolam with placebo," 38(3) Arzneimittelforschung 387-392 (Mar. 1988).
Kevin T. Bain, "Management of Chronic Insomnia in Elderly Persons," 4(2) Am. J. Geriatr. Pharmacother. 168-192 (Jun. 2006).
Bjarke Ebert et al., "Treating Insomnia: Current and Investigational Pharmacological Approaches," 112 Pharmacol. & Ther. 612-629 (2006).
Goodman and Gilman's: The Pharmacological Basis of Therapeutics (9th ed.), Chapter 17, pp. 363-365 (1996).
Robert Stickgold, "Sleep-Dependent Memory Consolidation," 437(27) Nature 1272-1278 (Oct. 2005).
Communication pursuant to Article 94(3) EPC in European Patent Application No. 08785624.1 (dated Sep. 2011).
Communication pursuant to Article 94(3) EPC in European Patent Application No. 08785624.1 (dated May 2011).
Communication pursuant to Article 94(3) EPC in European Patent Application No. 08785624.1 (dated Jul. 2010).
Second Office Action in Chinese Application No. 200880112316.2 (dated Jun. 13, 2012).
Office Action in Russian Application No. 2010110560 (dated Jun. 20, 2012).
M.M. Skugarevskaya, "Contemporary Approaches to Insomnia Therapy," Meditsinskie Novosti (Medical News), 2005, No. 10 [online] [retrieved Jun. 5, 2012] (URL <mednovosti.by/journal/aspx?article=1045).
C.G. Swift et al., "SingleDose Pharmacokinetics and Pharmacodynamics of Oral Loprazolam in the Elderly." 20(2) Br. J. Clin. Pharmacol. 119-128 (Aug. 1985).
Office Action in Japanese Application No. 2010-521352 (dated Apr. 2, 2013).
R. Gieschke et al., "Effects of Bretazenil vs. Zolpidem and Placebo on Experimentally Induced Sleep Disturbance in Healthy Volunteers," 16(9) Meth. Find. Exp. Clin. Pharmacol. 667-675 (1994).
International Preliminary Report on Patentability in Application No. PCT/EP2008/006810 (dated Feb. 24, 2010).
N. Stanley et al., "A Placebo Controlled, Randomised, Double-Blind, 4 Way Cross-Over Study of 3 Doses of EVT 201 on Aspects of Sleep and Morning After Performance Using a Traffic Noise Model of Sleep Disturbance", Journal of Sleep Research, vol. 15, No. suppl. 1, p. 40, 2006.
Final Rejection in Japanese Application No. 2010-521352 (dated Nov. 26, 2013).
Thomas Roth, "The Relationship Between Psychiatric Disease and Insomnia," Int. J. Clin. Pract., 2001; (Suppl.):3-8.
Russell P. Rosenberg et al., "Sleep Maintenance Insomnia: Strengths and Weaknesses of Current Pharmacologic Therapies," Annals of Clinical Psychiatry, 18[1]:49-56, 2006.
Paul J. Whiting, "GABA—A Receptor Subtypes in the Brain: A Paradigm for CNS Drug Discovery?" DDT, 8[10]:445-50 (May 2003).
Roland Baur et al., "Novel Plant Substances Acting as β Subunit Isoform-Selective Positive Allosteric Modulators of GABAA Receptors," Mol. Pharmacol. 68[3]:787-92 (2005).
Erwin Sigel et al., "The Effect of Subunit Composition of Rat Brain GABAA Receptors on Channel Function," Neuron 5:703-11 (Nov. 1990).
Enrico Sanna et al., "Comparison of the Effects of Zaleplon, Zolpidem, and Triazolam at Various GABAA Receptor Subtypes," Eur. J. Pharmacol. 451:103-10 (2002).
Pascale Abadie et al., "Central Benzodiazepine Receptor Occupancy by Zolpidem in the Human Brain as Assessed by Positron Emission Tomography," European Journal of Pharmacology, 295:35-44 (1996).
Mark R. Pressman, "Stages and Architecture of Normal Sleep," UpToDate Website (http://patients.uptodate.com/print.asp?print=true&file=sleepdis/8234) (Aug. 2007).
Timothy Roehrs et al., "The Effect of Drugs on Sleep Quality and Architecture," UpToDate Website (http://patients.uptodate.com/topic.asp?file=sleepdis/6893&title=Sleep+stages) (Aug. 2007).
Jadwiga Najib, "Eszopiclone, a Nonbenzodiazepine Sedative-Hypnotic Agent for the Treatment of Transient and Chronic Insomnia," Clinical Therapeutics, 28[4]:491-516 (Apr. 2006).
G. Hopfgartner et al., "High-Throughput Quantification of Drugs and Their Metabolites in Biosamples by LC-MS/MS and CE-MS/MS: Possibilities and Limitations," Therapeutic Drug Monitoring, 24:134-143 (2002).
P. Heizmann et al., "Application of LC-SIMS-MS in Drug Assay Development," Chromatographia, 52, Suppl., S-46-S-48 (2000).
Headline Results of First Study in Healthy Volunteers (Oct. 2005).
News Release: Positive Phase I/II Clinical Trial Results with Insomnia Treatment, pp. 1-2 (Jun. 2006).
News Release: Initiation of Phase II Clinical Trial for the Treatment of Insomnia, pp. 1-2 (Sep. 2006).
News Release: Initiation of Second Phase II Clinical Trial (Study in Elderly Patients with Primary Insomnia and Daytime Sleepiness), pp. 1-2 (Nov. 2006).
News Release: Positive Proof-of-Concept Top-Line Results with Insomnia Drug Candidate, pp. 1-4 (Jun. 2007).
R&D Seminar, pp. 59-82 (Mar. 2006).
R&D Seminar, pp. 59-91 (Feb. 2007).
First Phase II Results, pp. 2-11 (Jun. 2007).
Detailed Study Results, pp. 1-23 (Sep. 2007).
News Release: Details of the Positive Proof-of-Concept Phase II Study in Insomnia, pp. 1-4 (Sep. 2007).
N. Stanley et al., "A Placebo Controlled, Randomised, Double-Blind,4 Way Cross-Over Study of 3 Doses of EVT201 (2.5MG, 5MG and 10MG) on Aspects of Sleep and Morning After Performance Using a Traffic Noise Model of Sleep Disturbance", p. A285, Sleep, vol. 29, Abstract Supplement (2006).
J. Boyle et al., "A Placebo Controlled, Randomised, Double-Blind, 5 Way Cross-Over Study of 4 Doses of EVT 201 on Subjective Sleep Quality and Morning After Performance in a Traffic Noise Model of Sleep Disturbance," pp. A262-A263, Sleep,vol. 30, Abstract Supplement, 2007.
A.J. Boileau et al., "The Relative Amount of cRNA Coding for γ2 Subunits Affects Stimulation by Benzodiazepines in GABAA Receptors Expressed in Xenopus Oocytes," 2002; Neuropharmacology 43, 695-700.
Erwin Sigel, "Properties of Single Sodium Channels Translated by Xenopus Oocytes After Injection With Messenger Ribonucleic Acid," 1987; J. Physiol. 386, 73-90.
In focus, Issue No. 7, Dec. 2005, pp. 3-5.
In focus, Issue No. 8, Aug. 2006, pp. 3-7.
In focus, Issue No. 9, Feb. 2007, pp. 7-9.
In focus, Issue No. 10, Aug. 2007, pp. 3-5.
In focus, Issue No. 11, Mar. 2008, pp. 3 and 16.
Extended European Search Report in European Application No. 07114635.1 (dated Jan. 21, 2008).
Martin & Haefely, "Drugs Used for the Treatment of Anxiety and Sleep Disorders," pp. 243-277 (1995).
D. Wheatley, "Prescribing Short-Acting Hypnosedatives. Current Recommendations from a Safety Perspective," Drug Safety 1992; 7:106-115.
Extended European Search Report in European Application No. 07114634.1 (dated Jan. 30, 2008).
Evotec AG Annual Report 2005 Excerpts (2006).
Evotec AG, First Quarter Report 2006, pp. 1-3 (2006).
Evotec AG, Second Quarter Report 2006, pp. 1-4 (2006).
Evotec AG, Third Quarter Report 2006, pp. 1-3 (2006).
Evotec AG Annual Report 2006 Excerpts (2007).
Evotec AG, First Quarter Report 2007, pp. 1-4 (2007).
Evotec AG, Half Year Report 2007, pp. 1-3 (2007).
Evotec AG, Third Quarter Report 2007, pp. 1-3 (2007).
Evotec AG Annual Report 2007 Excerpts (2008).

(56) References Cited

OTHER PUBLICATIONS

Evotec AG, First Quarter Report 2008, pp. 1-4 (2008).
Evotec AG, Half-Year Report 2008, pp. 1-4 (2008).
Evotec AG Annual Report 2008 Excerpts (2009).
Office Action in Chinese Application No. 200880112316.2 (dated Jul. 7, 2011).
British National Formulary 54, pp. 18-19, 176-185 (2007).
FDA's Guidance for Industry: Content and Format for Geriatric Labeling, pp. 1-10 (Oct. 2001).
Notice of Preliminary Rejection in Korean Application No. 10-2010-7003698 (dated Jan. 13, 2015).
Office Action in Canadian Application No. 2,696,703 (dated Dec. 1, 2014).
First Examination Report in Indian Patent Application No. 1144/DELNP/2010 (dated Feb. 11, 2015).
Office Action in Canadian Application No. 2,696,703 (dated Jun. 23, 2015).
Leo E. Hollister et al., "Clinical Uses of Benzodiazepines," 13(6) (Suppl. 1) J. Clin. Psychopharmacol. 1S-169S (1993).
Unfavorable Opinion in Brazilian Application No. PI0815579-8 (published Aug. 7, 2018).
J.-M. Gaillard et al., "Effect of the Benzodiazepine Antagonist Ro 15-1788 on Flunitrazepam-Induced Sleep Changes," 15 Br. J. Clin. Pharmac. 529-536 (1983).
Timothy Roehrs et al., "The Effects of Medications on Sleep Quality and Sleep Architecture," Official Reprint from UpToDate (www.uptodate.com), pp. 1-7 (2013).
Matthew P. Walker, "The Role of Slow Wave Sleep in Memory Processing," 5(2) J. Clin. Sleep Med. (Suppl.) S20-S26 (2009).

\* cited by examiner

* Error bars represent 95% confidence interval

| Screening | Treatment Phase | Completion |
|---|---|---|
| Screening | Single blind placebo 2 nights | Double blind 1.5 mg, 2.5 mg or placebo 7 nights | Follow Up |
| Visit 1 Day -21 | Visit 2 Max Min Day -14 Day -5 | Visit 3 Day 1 | Patient sleeps at home Days 2-5 | Visit 4 Days 6-8 | Visit 5 Days 11-13 |

- Parallel group design (~ 45 patients per group)
- Days 1, 6 and 7 in Sleep laboratory, Days 2-5 at home
- Dosed at 30 minutes before lights out with PSG for 8 hours on nights 1, 6 and 7
- Rey Auditory Verbal Learning Test (RAVLT) pre sleep and 30 minutes post wake time
- Profile of Mood State (POMS) 3 and 7 hours post waking
- Karolinska Sleepiness Scale (KSS) + Psychomotor Vigilance Task (PVT) followed by MSLT from 2 hours post wake on day 8 throughout day

Fig. 17

TREATMENT OF SLEEP DISORDERS

BACKGROUND OF THE INVENTION

Field of the Invention

Insomnia is one of the most common complaints in general medical practice. Approximately 10% to 15% of adults suffer from chronic insomnia and an additional 25% to 35% have transient or short-term insomnia. Chronic insomnia is typically accepted to involve episodes greater than three (3) weeks in duration. Transient insomnia is an insomnia that is present for one to several days, and is less than one week in duration. Short-term insomnia is an insomnia of one to three weeks in duration (Roth, Int. J. Clin. Pract. 2001; (Suppl.):3-8).

Generally, as discussed in detail by Russell P. Rosenberg in "Sleep Maintenance Insomnia Strengths and Weaknesses of Current Pharmacologic Therapies," Annals of Clinical Psychiatry, 18[1]:49-56, 2006, which is incorporated herein by reference, patients with insomnia are also categorized according to when their sleep difficulty most often occurs. The three recognized categories of insomnia are (1) sleep onset insomnia (difficulty in falling asleep); (2) sleep maintenance insomnia (difficulty staying asleep); and (3) terminal insomnia (early-morning awakenings coupled with an inability to return to sleep). Terminal insomnia is sometimes referred to as sleep offset insomnia. These symptoms may occur singly or in combination, as is the case in many patients with chronic insomnia, which may result from several different etiologies. Patients often have several sleep complaints simultaneously and experience a gamut of sleep disturbances, including prolonged latency to sleep onset, increased time awake during the sleep period and reduced total sleep time.

There are various medications that have been used to treat insomnia. The early type of insomnia drugs are what have come to be known as classic benzodiazepines. These benzodiazepines exert their pharmacological actions by interacting with the benzodiazepine binding sites associated with the $GABA_A$ receptor. $GABA_A$ receptors are ligand-gated ion channels, and functional receptors are made up from combinations of different subunit proteins. Subunits are divided in three main classes of alpha ($\alpha$), beta ($\beta$) and gamma ($\gamma$) subunits. $GABA_A$ receptors that have a benzodiazepine binding site are formed from either $\alpha_1$, $\alpha_2$, $\alpha_3$ or $\alpha_5$ subunits in combination with $\beta$ and $\gamma_2$ subunits (Paul J. Whiting, DDT Vol. 8, No. 10, May 2003).

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects. However, while some classic benzodiazepines, which are considered full agonists at the $GABA_A$ receptor benzodiazepine site, are generally regarded as being effective at inducing and maintaining sleep, which is believed to be due to their relatively long half-lives ranging from 10-40 hours, they were found to produce undesirable residual effects. These may include cognitive impairment, excessive sedation, ataxia, potentiation of ethanol effects and a tendency for tolerance and drug dependence. A particular problem with classic benzodiazepines is rebound insomnia, manifested by restlessness and somnipathy, which emerges on withdrawal. Furthermore, the quality of sleep that is induced by these compounds is unphysiological. Classic benzodiazepines typically reduce slow wave sleep (SWS), rapid eye movement (REM) sleep and generally adversely affect sleep architecture. One of the reasons for these undesirable side effects was deemed to be associated with the afore-mentioned relatively long half-life of the classic benzodiazepines.

In order to overcome these problems, agents with shorter half-lives have been investigated. Examples of such agents include the so-called non-benzodiazepines, such as zolpidem and zaleplon, that also act as full agonists at the $GABA_A$ receptor benzodiazepine site. However, while these newer agents are generally effective in reducing time to sleep onset (i.e., decreasing sleep latency), they have been found to be less effective at improving sleep maintenance, as well as treating terminal insomnia.

Sleep maintenance difficulties can be quantified using Polysomnography (PSG). When quantifying sleep maintenance difficulties via PSG, wake after sleep onset (WASO) and number of awakenings (NAW) are the most commonly utilized parameters. WASO is a robust measure of sleep maintenance, as it represents the total amount of time spent awake after the onset of persistent sleep measured over a fixed 8-hour period in bed (captures total duration of lost sleep after at least 1 awakening), while NAW represents only the number of wake periods lasting at least 1 minute occurring after the onset of persistent sleep. Therefore, a person may wake only once during the night (NAW), but may spend 3 hours awake (WASO), so the latter measure more closely reflects the level of disturbance.

Difficulty with maintaining sleep is common in patients with medical and psychiatric disorders, as well as in patients with primary insomnia, and it occurs with more frequency than sleep onset problems in certain population groups. However, it is widely recognized that currently used medications fall short when it comes to safely and effectively addressing sleep maintenance problems.

An additional problem with conventionally known insomnia agents concerns the elderly population (at least 65 years old). The elderly insomnia population represents an important and underserved patient population. Sleep maintenance and terminal insomnia are more prevalent in the elderly population compared to younger patient populations (McCall et al. 2005; National Sleep Foundation, Sleep in America Poll 2005). Metabolism of many existing drugs for insomnia shows significant changes with age and so may necessitate a dose adjustment for elderly patients (McCall et al 2005). In the case of zolpidem (Ambien®) and modified release zolpidem (zolpidem-MR; Ambien CR®), indicated doses for the elderly (65 and over) are half those of non-elderly adults (18-64) due to increased exposure in the elderly. In the case of eszopiclone (Lunesta®), there is prolonged elimination with the half-life increasing from 6 hours in non-elderly adults to 9 hours in the elderly. Such an increase in half-life raises the likelihood of accumulation and carry-over effects after repeat dosing in the elderly. Furthermore, these changes in metabolism with age are gradual and vary between individuals. Therefore, it is more difficult to select an appropriate dose of drugs undergoing metabolism that is sensitive to age-related changes.

SUMMARY OF THE INVENTION

The present invention provides an effective method for treating sleep maintenance insomnia and/or terminal insomnia, each of which can be associated with transient, short-term, chronic, primary and secondary insomnia. Specifically, the present invention provides a method for decreasing wake after sleep onset (WASO), increasing total sleep time (TST), reducing total wake time, particularly in the second half of the night, and/or reducing early-morning awakenings. Also, the present invention improves daytime function in the elderly. One or more of these advantages can be achieved while reducing latency to sleep onset and/or latency to persistent sleep, thus also effectively treating sleep onset insomnia. Accordingly, the present invention provides an effective compound for treating various types of insomnia, including insomnia in the elderly population.

The compound is 7-chloro-3-(5-dimethylaminomethyl-[1,2,4]oxadiazol-3-yl)-5-methyl-4,5-dihydro-imidazo[1,5-a][1,4]benzodiazepine-6-one, which is represented by formula (II) below, or a pharmaceutically acceptable salt thereof

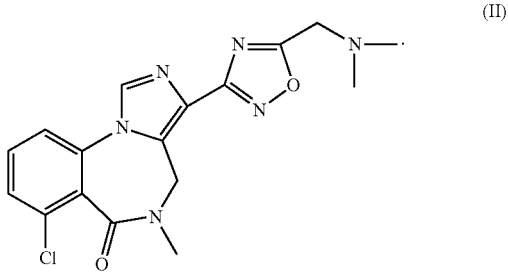 [SMILES: CN(C)Cc1nc(-c2ncn3c2CN(C)C(=O)c2c(Cl)cccc2-3)no1]

(II)

In particular, in one aspect, the present invention provides a use of a compound of formula (II) or a pharmaceutically acceptable salt thereof in the preparation of a medicament for any of treating maintenance insomnia and/or terminal insomnia, as well as sleep onset insomnia, each of which can be associated with transient, short-term, chronic, primary and secondary insomnia by, for example, decreasing wake after sleep onset (WASO), increasing total sleep time (TST), reducing total wake time, particularly in the second half of the night, and/or reducing early-morning awakenings.

Preferably, the present invention provides a use of a compound of formula (II) or a pharmaceutically acceptable salt thereof in the preparation of a medicament for increasing total sleep time in a period from about four to about eight hours, more preferably from about five to about eight hours, yet more preferably from about six to about eight hours after the administration of the medicament. The start and end of this period are measured from the administration of the effective amount of the medicament or from the administration of a partial amount, presuming that dosing of the effective amount of the medicament is completed.

Preferably, the present invention provides a use of a compound of formula (II) or a pharmaceutically acceptable salt thereof in the preparation of a medicament for decreasing wake after sleep onset in a period from about four to about eight hours, more preferably from about five to about eight hours, yet more preferably from about six to about eight hours after the administration of the medicament. The start and end of this period are measured from the administration of the effective amount of the medicament or from the administration of a partial amount, presuming that dosing of the effective amount of the medicament is completed.

Preferably, the amount of the compound of formula (II) or its pharmaceutically acceptable salt that is administered for the treatment is from about 0.5 mg to about 5 mg. The treatment amount may be from about 1.0 mg to about 4.5 mg, from about 1.5 mg to about 4 mg, from about 2 mg to about 3.5 mg, from about 2.5 mg to about 3 mg, or any range among all of the above-listed amounts. For example, the treatment amount is from about 0.5 mg or about 1.5 mg to about 5 mg, about 4.5 mg, about 4 mg, about 3.5 mg, about 3 mg or about 2.5 mg. More preferably, the amount is from about 1 mg to about 3 mg, yet more preferably from about 1.5 mg to about 2.5 mg.

Accordingly, a particularly preferred pharmaceutical composition for the treatment in accordance with the present invention contains from about 0.5 mg to about 5 mg of the compound of formula (II) or a pharmaceutically acceptable salt thereof. More preferably, the pharmaceutical composition will be in a unit dosage form comprising 0.5 mg, 1 mg, 1.5 mg, 2 mg, 2.5 mg, 3 mg, 3.5 mg, 4 mg, 4.5 mg or 5 mg of the compound of formula (II) or a pharmaceutically acceptable salt thereof.

The onset, maintenance and/or terminal insomnia may be treated by, for example, decreasing wake after sleep onset (WASO), increasing total sleep time (TST), reducing total wake time, particularly in the second half of the night, and/or reducing early-morning awakenings, by administering the compound of formula (II) or a pharmaceutically acceptable salt thereof to achieve an AUC from about 17.5 ng·h/mL to about 600 ng·h/mL, from about 25 ng·h/mL to about 500 ng·h/mL or from about 25 ng·h/mL to about 400 ng·h/mL. For example, the AUC may be from about 52.5 ng·h/mL to about 360 ng·h/mL, from about 75 ng·h/mL to about 300 ng·h/mL, from about 75 ng·h/mL to about 240 ng·h/mL, from about 75 ng·h/mL to about 200 ng·h/mL, from about 75 ng·h/mL to about 150 ng·h/mL, from about 105 ng·h/mL to about 120 ng·h/mL, or any range among all of the above-listed AUC values. Preferably, the AUC is from about 75 ng·h/mL to about 240 ng·h/mL.

The treatment is also conducted to achieve a $C_{max}$ from about 2.5 ng/mL to about 125 ng/mL, from about 7.5 ng/mL to about 75 ng/mL, from about 7.5 ng/mL to about 62.5 ng/mL, from about 7.5 ng/mL to about 37.5 ng/mL, from about 10 ng/mL to about 50 ng/mL, from about 12.5 ng/mL to about 45 ng/mL, from about 15 ng/mL to about 40 ng/mL, or any range among all of the above-listed $C_{max}$ values. Preferably, the $C_{max}$ is from about 15 ng/mL to about 45 ng/mL.

The subjects to be treated in accordance with the present invention are humans.

As used herein, "adults" are humans who are at least 18 years old. The "non-elderly" are adult humans who are 18 to 64 years old. The "elderly" are adult humans who are at least 65 years old.

As used herein, "primary insomnia" is sleeplessness that is not attributable to a medical, psychiatric, or environmental cause. The diagnostic criteria for primary insomnia may be found in the *Diagnostic and Statistical Manual of Mental Disorders*, Fourth Edition (DSM-IV), which is incorporated herein by reference.

As used herein, "secondary insomnia" is insomnia in which a specific medical, psychiatric, or environmental condition can be identified as the cause of the sleep problem.

Transient insomnia is an insomnia that is present for one to several days, and is less than one week in duration. Short-term insomnia is an insomnia of one to three weeks in duration. Chronic insomnia is typically accepted to involve episodes greater than three (3) weeks in duration. (Roth, Int. J. Clin. Pract. 2001; (Suppl.):3-8).

Sleep onset or onset insomnia is insomnia, which is characterized by difficulty in falling asleep. Maintenance insomnia is insomnia, which is characterized by difficulty staying asleep. Terminal or offset insomnia is insomnia, which is characterized by early-morning awakenings coupled with an inability to return to sleep.

As used herein, latency to persistent sleep (LPS) is defined as the time from "lights out" to the beginning of 10 uninterrupted minutes of sleep.

Persistent sleep is defined as 10 uninterrupted minutes of sleep after initial sleep onset.

Wake after sleep onset (WASO) is defined as the total amount of time spent awake after the onset of persistent sleep measured over a fixed 8-hour period in bed (captures total duration of lost sleep after at least 1 awakening). "sWASO" refers to the subjective WASO as reported by individuals.

Total wake time (TWT) is defined as the total amount of time spent awake measured over a specific period of time.

Number of awakenings (NAW) is defined as the return to an awake state (number of wake periods lasting at least 1 minute occurring after the onset of persistent sleep). "sNAW" refers to the subjective NAW as reported by individuals.

Total sleep time (TST) is defined as the total time asleep measured over a fixed 8-hour period. As shown herein, an increase in TST achieved by the administration of the compound of formula (II) or a pharmaceutically acceptable salt thereof is not dependent on a reduction in time to sleep onset. "sTST" refers to the subjective TST as reported by individuals.

Sleep efficiency index is a ratio of TST to total time in bed, i.e., a percentage of time spent asleep. Total time in bed is typically 8 hours for study purposes.

Sleep architecture refers to the changes in the stages of sleep during the sleep period. Typically, in healthy humans, sleep stages occur in cycles lasting about 90 to about 120 minutes each. Four to five such cycles occur during a typical night of sleep. During the first half of the night, the healthy individual typically passes from wakefulness briefly into stage I sleep and then to stages II, III, and IV. Stages II and III reappear, after which rapid eye movement (REM) sleep is observed for the first time. During the second half of the night, stage II and REM sleep alternate.

Slow wave sleep (SWS) is stage III and IV sleep. It is characterized by a transition to an electroencephalogram (EEG) with high amplitude delta EEG waves (1.5 to 3 Hz).

As used herein, AUC is the area under the drug plasma concentration versus time curve from time zero to infinity. $C_{max}$ is the maximum observed plasma concentration of the drug from time zero to infinity.

BRIEF DESCRIPTION OF THE DRAWINGS

FIG. 17 shows the study design used in Example 4.

DETAILED DESCRIPTION OF THE INVENTION

Figure 1:
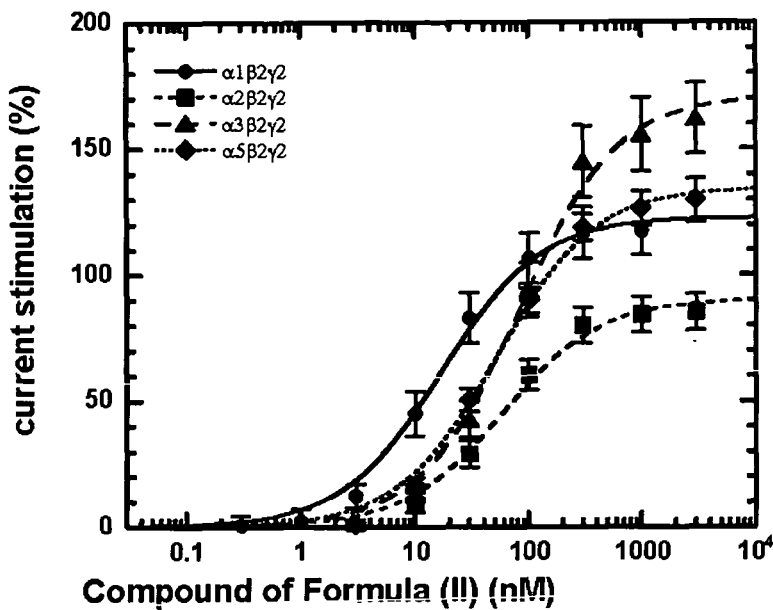
FIG. 1 is a plot showing concentration-dependent stimulation of currents elicited by GABA ($EC_{3-5}$) by the compound of formula (II) at $\alpha_1\beta_2\gamma_2$, $\alpha_2\beta_2\gamma_2$, $\alpha_3\beta_2\gamma_2$ and $\alpha_5\beta_2\gamma_2$ $GABA_A$ receptors expressed in Xenopus oocytes. Data is shown as mean±SEM.
Figure 2:
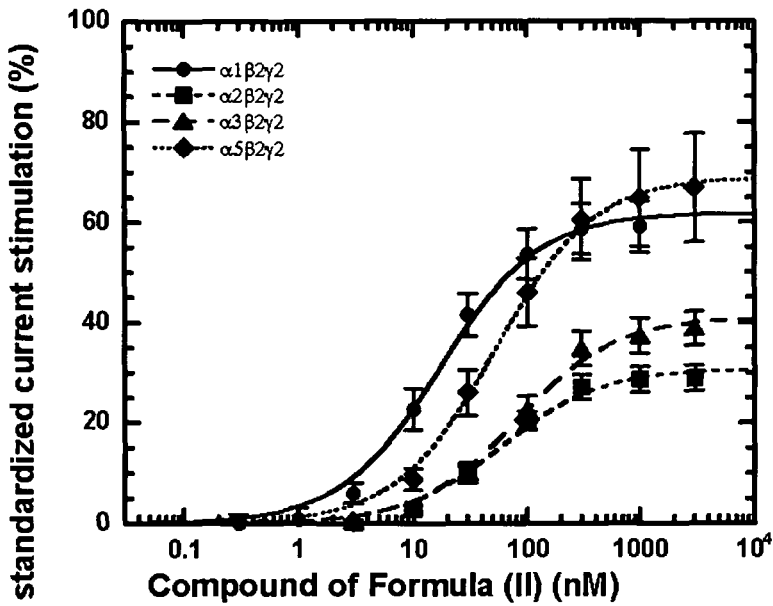
FIG. 2 is a plot showing concentration-dependent stimulation of currents elicited by GABA ($EC_{3-5}$) by the compound of formula (II) at $\alpha_1\beta_2\gamma_2$, $\alpha_2\beta_2\gamma_2$, $\alpha_3\beta_2\gamma_2$ and $\alpha_5\beta_2\gamma_2$ $GABA_A$ receptors expressed in Xenopus oocytes. Stimulation is standardized to the one observed using 1 μM diazepam in the same batch of oocytes. Data is shown as mean±SEM.

One of the major challenges in treating insomnia is to develop a drug that induces sleep quickly, helps individuals remain asleep and allows them to awaken feeling refreshed rather than hung over. Furthermore, with respect to the elderly, there is an additional challenge to develop a drug with a metabolism that is largely unaffected by the aging process.

The present invention addresses one or both of these challenges. In particular, the present invention provides a use of a compound of formula (II) or a pharmaceutically acceptable salt thereof in preparation of a medicament for treating the sleep onset, maintenance and/or terminal insomnia by, for example, decreasing wake after sleep onset (WASO), increasing total sleep time (TST), reducing total wake time (TWT), particularly in the second half of the night, and/or reducing early-morning awakenings, in a human in need thereof:

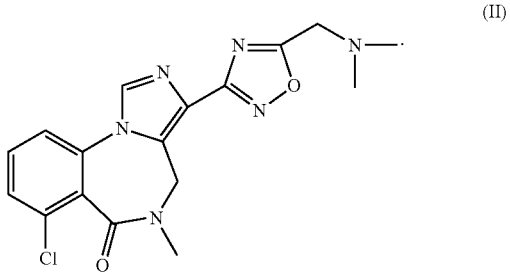 [SMILES: CN(C)Cc1nc(-c2ncn3c2CN(C)C(=O)c2c(Cl)cccc2-3)no1]

(II)

An effective amount of the compound of formula (II) or its pharmaceutically acceptable salt is administered to the patient in need of the treatment.

The compound of formula (II) can be prepared in accordance with the methods described in U.S. Pat. No. 6,391,873, which is incorporated herein by reference. It has been disclosed as useful for treating acute and chronic anxiety disorders.

As disclosed in U.S. Pat. No. 5,665,718, this type of compound is deemed to display sedative activity that sets in very rapidly, but lasts only a relatively short period of time. Accordingly, the compound of formula (II) or a pharmaceutically acceptable salt thereof would not be expected to be beneficial in the treatments of maintenance and terminal insomnia, much more so in the elderly who are generally expected to react differently than other adults to insomnia medication.

Nonetheless, the compound of formula (II) or a pharmaceutically acceptable salt thereof was surprisingly found to be effective for treatment of not only sleep onset insomnia, but also maintenance insomnia and terminal insomnia in humans, including the elderly, even when the administration amount was significantly low, on the order of about 0.5 mg to about 5 mg, particularly from about 1.5 mg to about 2.5 mg. The surprising nature of these results is further supported by the finding that the compound of formula (II) has a relatively short half-life of about 3-4 hours, akin to the conventional insomnia treatment agents having relatively short half-lives, which were found lacking effectiveness in sleep maintenance. The efficacy of the compound of formula (II) for the treatment of various types of insomnia was not found to be improved when the administration amount exceeded about 5 mg, and residual sedation effects were noted at higher doses in non-elderly adults. Conventional insomnia agents, such as zolpidem, trazodone and zaleplon, were found to be less effective for treating maintenance and terminal insomnia even when administered in amounts that are at least twice that of the compound of formula (II) or a pharmaceutically acceptable salt thereof. Furthermore, conventional insomnia medications agents tend to produce excessive residual sedative effects in the elderly, exacerbating excessive daytime sleepiness, which the elderly already tend to experience due to lack of sleep during nighttime.

Pharmaceutically acceptable salts for the compound of formula (II) can be prepared by standard techniques that will be familiar to the person skilled in the art. Suitable pharmaceutically acceptable salts are acid addition salts, such as those with inorganic or organic acids. Examples of these salts are the hydrochlorides, hydrobromides, sulfates, nitrates, citrates, acetates, maleates, succinates, methanesulphonates, p-toluenesulphonates and the like.

The compound of formula (II) or a pharmaceutically acceptable salt thereof achieves its sedative effects by positive allosteric modulation of $GABA_A$ receptors via the benzodiazepine site. However, unlike conventional agents for treating insomnia that act at the benzodiazepine site, the compound of formula (II) or a pharmaceutically acceptable salt thereof is only a partial agonist, i.e., it produces a lower maximum potentiation of the $GABA_A$ receptor. Thus, unexpectedly, it was found that even a partial agonist can be used for the treatment of maintenance and terminal insomnia. Furthermore, surprisingly, it was found that the compound of formula (II) or a pharmaceutically acceptable salt thereof can be used to treat insomnia in the elderly within the same dosage range as needed for other adults and improved daytime function for the elderly who suffer from daytime sleepiness.

The ability to allosterically stimulate currents elicited by GABA ($EC_{3-5}$) was determined for the compound of formula (II), zolpidem and diazepam at the rat $GABA_A$ receptors of the subunit composition $\alpha_1\beta_2\gamma_2$, $\alpha_2\beta_2\gamma_2$, $\alpha_3\beta_2\gamma_2$ and $\alpha_5\beta_2\gamma_2$. 7-Chloro-3-(5-dimethylaminomethyl-[1,2,4]oxadiazol-3-yl)-5-methyl-4,5-dihydro-imidazol[1,5,-a][1,4]benzodiazepine-6-one was used to test the effects of the compound of formula (II):

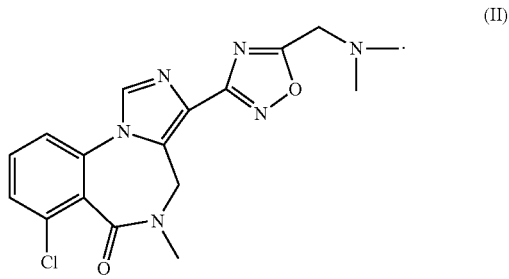 [SMILES: CN(C)Cc1nc(-c2ncn3c2CN(C)C(=O)c2c(Cl)cccc2-3)no1]

(II)

Similar procedures were chosen as for the investigation of other $GABA_A$ receptor subunit specific substances (e.g., Baur et al., 2005; Mol. Pharmacol. 68, 787-792).

Expression in *Xenopus* Oocytes

Lobes of the ovary containing the follicles were obtained by surgical procedures from female *Xenopus laevis*. Follicles were singled out using a platinum loop. Fifty nL of cRNA solution at a ratio of $\alpha_x:\beta_2:\gamma_2$ of 1:1:5 (3.3-10 nM $\alpha_x$ (x=1, 2, 3, 5); 3.3-10 nM $\beta_2$; 16.7-50 nM $\gamma_2$) (Boileau et al., 2002; Neuropharmacology 43, 695-700) were microinjected into *Xenopus* follicles. Several hours after microinjection the follicles were freed of follicular layers and adhering connective tissue by a collagenase/hypertonic shock procedure (Sigel, 1987; J. Physiol. (Land) 386, 73-90). Oocytes were kept at constant 18° C. until measurement (1-4 days) in a modified Barth solution (88 mM NaCl, 1 mM KCl, 2.4 mM $NaHCO_3$, 10 mM Hepes-NaOH (pH 7.5), 0.82 mM MgSO$_4$×7H$_2$O, 0.34 mM Ca(NO$_3$)$_2$×4H$_2$O, 0.41 mM CaCl$_2$×2H$_2$O, 100 U Penicillin/mL, 100 µg Streptomycin/mL, sterile filtered).

Electrophysiological Investigation

Currents were measured using a home-built amplifier in combination with a xy-recorder or were digitized using a MacLab/200 (AD Instruments) and stored on a computer. *Xenopus* oocytes were voltage clamped using the two-electrode voltage clamp technique (electrode resistance about 0.8 MΩ) at −80 mV. The medium contained 90 mM NaCl, 1 mM KCl, 1 mM MgCl$_2$, 1 mM CaCl$_2$, 10 mM Na-Hepes (pH 7.4) and 0.5% DMSO.

GABA was applied for 20-50 seconds without or in combination with other drugs and a washout period of 4 minutes was allowed to ensure full recovery from desensitization, which was experimentally determined. The perfusion solution (6 mL/min) was applied through a glass capillary with an inner diameter of 1.35 mm, the mouth of which was placed about 0.4 mm from the surface of the oocyte. The rate of solution change under our conditions has been estimated 70% within less than 0.5 s (Sigel et al., 1990; Neuron 5, 703-711). The entire perfusion system and the assay chamber were cleaned between drug applications by washing with DMSO.

Data Handling

Data is given as mean±SD, except in the figures where data is shown for clarity as mean±SEM. Current stimulation was calculated as follows: stimulation (%)= ((I$_{(GABA+modulator)}$−I$_{(GABA)}$)/I$_{(GABA)}$)×100%, where I is the current amplitude. Where indicated, the stimulation was standardized to the stimulation by 1 µM diazepam (100%). To obtain FIGS. 1-4, values for current stimulation obtained at a given concentration of modulator at a given subunit combination were averaged. The data points were fitted with the equation stimulation=efficacy/(1+(potency/concentration of modulator)). The values given in the Tables (Summary) are obtained by fitting individual curves and subsequently averaging efficacy and potency.

Results

Compound of Formula (II)

GABA (EC$_{3-5}$) was applied to an oocyte expressing α$_1$β$_2$γ$_2$ GABA$_A$ receptors several times until the current response was stable. The GABA (EC$_{3-5}$) refers to the effective concentration of GABA, which produces a response that is 3-5% of the maximal response to high concentrations of GABA. Such a low concentration of GABA is chosen in order to better see the potentiating effect of positive allosteric modulators.

GABA was then applied in combination with various concentrations of the compound of formula (II) between 0.3 nM and 3,000 nM to produce a cumulative concentration response curve. This resulted in a concentration-dependent potentiation of the GABA response as plotted in FIGS. 1 and 2. In each batch of oocytes the stimulation by 1 µM diazepam was determined in five oocytes, extent of stimulation averaged and defined as 100%. Where indicated, stimulation by the compound of formula (II) in each batch of oocytes was expressed as a percentage of this value in the corresponding batch.

Concentration response curves were also performed with oocytes expressing α$_2$β$_2$γ$_2$, α$_3$β$_2$γ$_2$, or α$_5$β$_2$γ$_2$, after establishing the optimal concentration range as indicated above. The compound of formula (II) performed as a partial positive allosteric modulator. At concentrations <100 nM, the compound of formula (II) showed preference for α$_1$β$_2$γ$_2$ GABA$_A$ receptors in comparison to □α$_5$β$_2$γ$_2$, α$_3$β$_2$γ$_2$ and α$_2$β$_2$γ$_2$. FIG. 1 shows the dose dependent stimulation of currents elicited by GABA at α$_1$β$_2$γ$_2$, α$_2$β$_2$γ$_2$, α$_3$β$_2$γ$_2$, and α$_5$β$_2$γ$_2$ before and FIG. 2 after standardization to the stimulation by 1 µM diazepam (100%). Averaged data of the individual curves summarizing the effects of the compound of formula (II) are shown below for unstandardized and standardized stimulation.

TABLE 1

Summary for Compound of Formula (II)

| Receptor | Potency | Efficacy | Standardized Efficacy |
|---|---|---|---|
| α$_1$β$_2$γ$_2$ | 18 ± 6 nM (n = 4) | 123 ± 19% (n = 4) | 62 ± 10% (n = 4) |
| α$_2$β$_2$γ$_2$ | 62 ± 21 nM (n = 5) | 90 ± 16% (n = 5) | 31 ± 6% (n = 5) |
| α$_3$β$_2$γ$_2$ | 84 ± 15 nM (n = 5) | 171 ± 33% (n = 5) | 41 ± 8% (n = 5) |
| α$_5$β$_2$γ$_2$ | 53 ± 6 nM (n = 5) | 135 ± 16% (n = 5) | 69 ± 23% (n = 5) |

Zolpidem

GABA (EC$_{3-5}$) was applied to an oocyte expressing α$_1$β$_2$γ$_2$ GABA$_A$ receptors several times until the current response was stable. Subsequently, GABA was applied in combination with various concentrations of zolpidem between 1 and 10,000 nM. Concentration response curves were performed twice with the same batch of oocytes and twice with an independent batch of oocytes.

In each batch of oocytes the stimulation by 1 µM diazepam was determined in five oocytes, extent of stimulation averaged and defined as 100%. Where indicated, stimulation by zolpidem in each batch of oocytes was expressed as percentage of this value in the corresponding batch.

Figure 3:
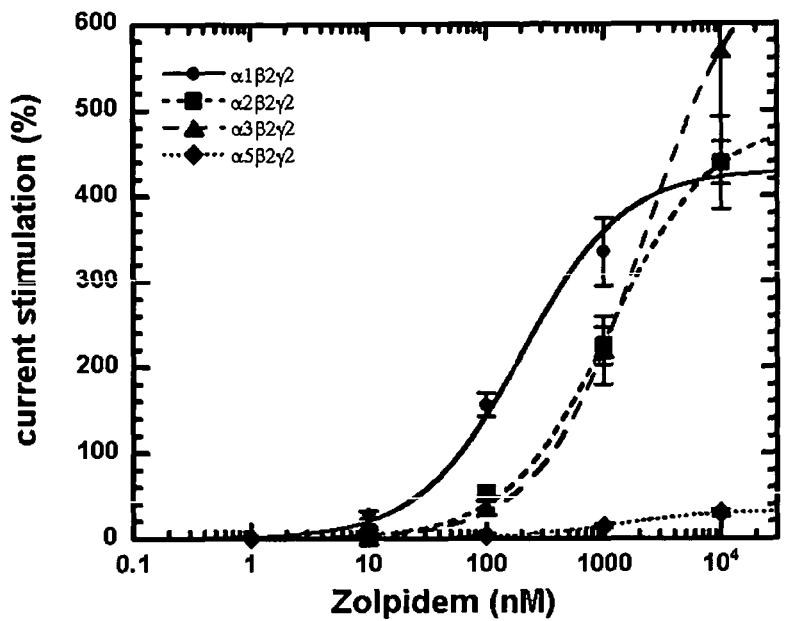
FIG. 3 is a plot showing concentration-dependent stimulation of currents elicited by GABA ($EC_{3-5}$) by zolpidem at $\alpha_1\beta_2\gamma_2$, $\alpha_2\beta_2\gamma_2$, $\alpha_3\beta_2\gamma_2$ and $\alpha_5\beta_2\gamma_2$ $GABA_A$ receptors expressed in Xenopus oocytes. Data is shown as mean±SEM.
Figure 4:
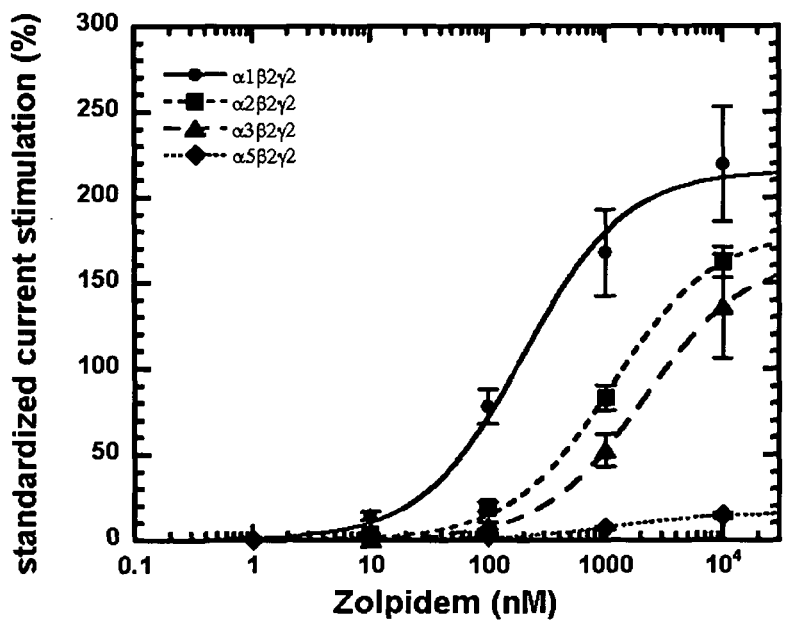
FIG. 4 is a plot showing concentration-dependent stimulation of currents elicited by GABA ($EC_{3-5}$) by zolpidem at $\alpha_1\beta_2\gamma_2$, $\alpha_2\beta_2\gamma_2$, $\alpha_3\beta_2\gamma_2$ and $\alpha_5\beta_2\gamma_2$ $GABA_A$ receptors expressed in Xenopus oocytes. Stimulation is standardized to the one observed using 1 μM diazepam in the same batch of oocytes. Data is shown as mean±SEM.

Concentration response curves were also performed with oocytes expressing α$_2$β$_2$γ$_2$, α$_3$β$_2$γ$_2$, or α$_5$β$_2$γ$_2$. As expected, zolpidem showed a higher affinity at α$_1$β$_2$γ$_2$ GABA$_A$ receptors in comparison to α$_2$β$_2$γ$_2$, α$_3$β$_2$γ$_2$, and α$_5$β$_2$γ$_2$. FIG. 3 shows the dose dependent stimulation of currents elicited by GABA at α$_1$β$_2$γ$_2$, α$_2$β$_2$γ$_2$, α$_3$β$_2$γ$_2$, and α$_5$β$_2$γ$_2$ before and FIG. 4 after standardization to the stimulation by 1 µM diazepam (100%). Qualitatively similar data have been published before (Sanna et al. 2002; Eur. J. Pharmacol. 451, 103-110). Averaged data of the individual curves summarizing the effects by zolpidem are shown below for unstandardized and standardized stimulation.

TABLE 2

Summary for Zolpidem (n = 5 each)

| Receptor | Potency | Efficacy | Standardized Efficacy |
|---|---|---|---|
| α$_1$β$_2$γ$_2$ | 191 ± 34 nM | 429 ± 120% | 215 ± 74% |
| α$_2$β$_2$γ$_2$ | 1135 ± 312 nM | 484 ± 60% | 179 ± 23% |
| α$_3$β$_2$γ$_2$ | 2021 ± 495 nM | 691 ± 365% | 166 ± 88% |
| α$_5$β$_2$γ$_2$ | 1260 ± 744 nM | 33 ± 12% | 16 ± 4% |

Diazepam

Current stimulation by diazepam was determined in each batch of oocytes as follows. GABA (EC$_{3-5}$) was applied until a stable response was obtained. Subsequently, GABA was applied in combination with 1 µM diazepam. Stimulation at the same subunit combination in different batches of oocytes was not statistically different, in each case. Stimulation by 1 µM diazepam at α$_1$β$_2$γ$_2$ amounted to 223±28% (n=5) and 178±20% (n=5) in two different batches of oocytes. Stimulation at α$_2$β$_2$γ$_2$ amounted to 264±61% (n=5), 280±71% (n=5) and 318±62% (n=5) in three different batches of oocytes. Stimulation at α$_3$β$_2$γ$_2$ amounted to 417±85% (n=5) and 417±144% (n=5) in two different batches of oocytes. Stimulation at $\alpha_5\beta_2\gamma_2$ amounted to 237±97% (n=5) and 160±4% (n=5) in two different batches of oocytes.

The results obtained for zolpidem are comparable to those achieved by Sanna et al 2002 (referenced above) in previous experiments and show an efficacy of 215% relative to diazepam at $\alpha_1\beta_2\gamma_2$ GABA$_A$ receptors. Zolpidem therefore acts as a positive allosteric modulator with high intrinsic activity, i.e., acts a full agonist. The compound of formula (II) showed a lower intrinsic activity, i.e., acts as a partial agonist.

Low intrinsic activity of the compound of formula (II) means that potentiation of the response mediated by GABA$_A$ receptors is limited even at high levels of receptor occupancy, which could be achieved with high concentrations of the compound of formula (II). PET studies indicate zolpidem (20 mg) produces receptor occupancy of about 20% in man (Abadie et al., European Journal of Pharmacology, 295 (1996), 35-44), i.e., clinical dose (10 mg) is on the steep inflection part of the dose-response curve. The compound of formula (II), nevertheless, still produces sufficient potentiation of the GABA$_A$ receptor to be highly effective for both sleep onset and maintenance. Excessive potentiation at higher doses is limited.

Producing lower stimulation at the individual receptor level is believed to be advantageous. Since the maximal potentiation of the GABA$_A$ response produced by such a low efficacy agonist is limited by its intrinsic efficacy, no further potentiation of the GABA$_A$ response is achieved beyond a certain plasma concentration. In a clinical setting, such a limit on the maximum potentiation of the GABA$_A$ receptor mediated response provides an advantageous ability to avoid excess potentiation with increasing plasma concentrations.

As a result of partial agonist activity at the GABA$_A$ receptor benzodiazepine site, the compound of formula (II) or a pharmaceutically acceptable salt thereof can also provide a more restful and improved quality of sleep by generally preserving sleep architecture. Classic benzodiazepines, which act as full agonists, typically reduce SWS and generally adversely affect sleep architecture. This ability to produce improved quality sleep over a sustained period, whilst minimizing side effects, leads to the advantageous use of the compound of formula (II) or a pharmaceutically acceptable salt thereof for the treatment of various types of insomnia. In particular, various types of insomnia may be treated advantageously by achieving a maximal potentiation of the response mediated by the $\alpha_1$ subunit containing GABA$_A$ receptors from only about 40% to about 90% using the compound of formula (II) or a pharmaceutically acceptable salt thereof.

The potentiation of the GABA$_A$ mediated response over time following the administration (e.g., oral) of the compound of formula (II) or a pharmaceutically acceptable salt thereof may be determined using a model. In this model, measured or predicted free plasma concentration following the dosing of the compound of formula (II) or a pharmaceutically acceptable salt thereof (assuming 50% plasma protein binding) as the clinically relevant drug concentration and the in vitro concentration-response data for GABA$_A$ receptor potentiation as discussed above can be used to predict the percent potentiation of the response mediated by GABA$_A$ $\alpha_1\beta_2\gamma_2$ ($\alpha_1$-containing) receptors over time after the administration. Specifically, the percent potentiation of the GABA$_A$ $\alpha_1\beta_2\gamma_2$ receptor mediated response for the compound of formula (II) or a pharmaceutically acceptable salt thereof can be calculated as follows:

% potentiation=Efficacy(maximal % potentiation of GABA$_A\alpha_1\beta_2\gamma_2$ receptor)/[1+(EC50/concentration of the compound of formula (II) or a pharmaceutically acceptable salt thereof)].

The compound of formula (II) and/or a pharmaceutically acceptable salt thereof can be used as medicaments, for example in the form of pharmaceutical preparations. The pharmaceutical preparations are typically administered orally, for example, in the form of tablets, coated tablets, dragées, hard and soft gelatine capsules, solutions, emulsions or suspensions. The administration can, however, also be effected rectally, for example, in the form of suppositories, or parenterally, for example, in the form of injection solutions.

The compound of formula (II) and/or a pharmaceutically acceptable salt thereof can be processed with pharmaceutically inert, inorganic or organic carriers for the production of pharmaceutical preparations, and the like. Lactose, corn starch or derivatives thereof, talc, stearic acid or its salts and the like can be used, for example, as carriers for tablets, coated tablets, dragées and hard gelatine capsules. Suitable carriers for soft gelatine capsules are, for example, vegetable oils, waxes, fats, semi-solid and liquid polyols and the like; although carriers are not necessary in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble acid addition salts of the compound of formula (II), but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

The compound of formula (II) or a pharmaceutically acceptable salt thereof is preferably administered in the amount from about 0.5 mg to about 5 mg. More preferably, the administration amount is from about 1 mg to about 3 mg, even more preferably from about 1.5 mg to about 2.5 mg. The drug is preferably administered once daily in an oral dosage form shortly before the patient wants to sleep. The oral dosage may consist of one or more tablets, coated tablets, dragées, hard and soft gelatine capsules, solutions, emulsions or suspensions and the like, so long as the desired amount of the medication is administered. Also, if desired, the daily dose may be administered in parts over a span of up to about 30 minutes.

Figure 16:
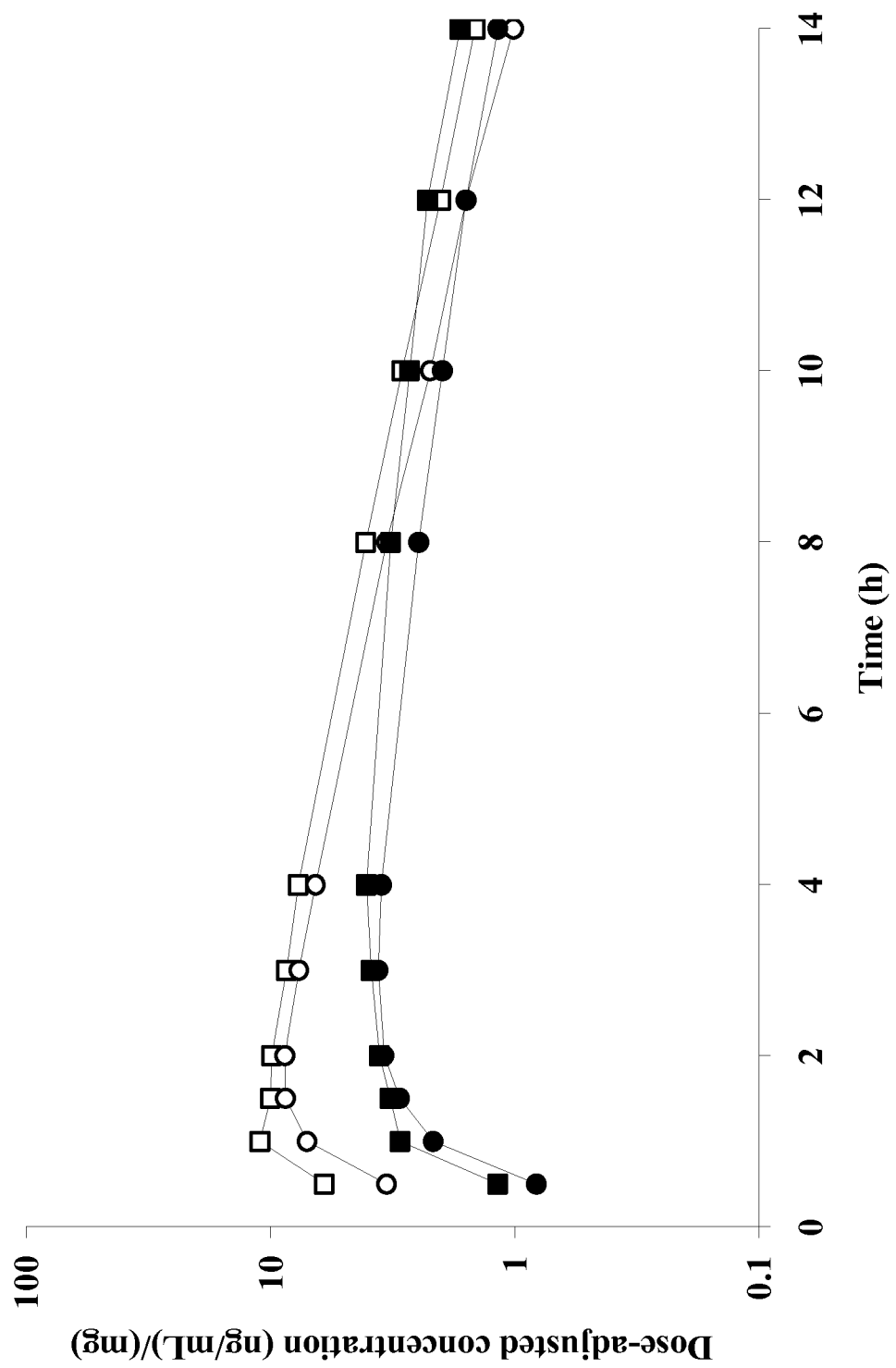
FIG. 16 is a chart showing an exemplary pharmacokinetic (PK) profile of the compound of formula (II) (free base) in both the non-elderly adults and the elderly. Mean dose adjusted plasma concentrations of the compound of formula (II) (free base) in non-elderly (open circle) and elderly males (open square) and M1 (active metabolite of the compound of formula (II) (free base)) in non-elderly adults (filled circle) and the elderly (filled square).

The inventors have determined that the compound of formula (II) shows similar pharmacokinetic (PK) profile in both the non-elderly and elderly, and exhibits less increase in exposure in the elderly than seen with zolpidem, and less increase in half-life than seen with eszopiclone, as shown in FIG. 16. As a result, the inventors determined that the same or similar doses of the compound of formula (II), which are effective for non-elderly adults (18-64 years of age), could be effective for the elderly.

The present invention is further described by the following Examples. These Examples are intended to illustrate some of the embodiments of the present invention and are not to be construed as limitations thereon.

Example 1

A placebo controlled, randomized, double-blind, crossover study of the effects of the compound of formula (II) was conducted using a road noise model using 12 healthy volunteers. Specifically, the volunteers were subjected to road traffic noise to imitate the effects of insomnia, and the medication was orally administered 5 minutes before the 11 pm bed time in 1.0 mg, 1.5 mg, 2 mg and 2.5 mg doses in the form of a hard gelatine capsule containing the powdered compound of formula (II) in free base form. Measurements were then taken at 8, 10 and 12 hours after dosing.

The results of the study are summarized in Tables 3-5.

TABLE 3

Objective Efficacy

| | | |
|---|---|---|
| Sleep Maintenance | WASO, full night (hrs 0-8) | Significantly reduced (1.5, 2.0 & 2.5 mg) |
| | WASO, 2$^{nd}$ half (hrs 5-8) | Significantly reduced (1.5, 2.0 & 2.5 mg) |
| | TST | Significantly improved (2.0 & 2.5 mg) |
| | Sleep Efficiency Index | Significantly improved (2.0 & 2.5 mg) |
| Sleep Architecture | SWS (% and duration) | Significantly increased (all 4 doses) |
| | Stage IV Sleep (% and duration) | Significantly increased (all 4 doses) |

TABLE 4

Subjective Efficacy

| | | |
|---|---|---|
| Leeds Sleep Evaluation Questionnaire | Quality of sleep | Significantly improved at all 4 doses |
| | Getting to sleep | (No effect to all 4 doses)* |
| | Ease of awakening | No effect (all 4 doses) |
| | Early morning behaviour (clumsiness & tiredness) | No effect (all 4 doses) |

*The road traffic noise model is considered clinically nondiscriminant for sleep onset measures

TABLE 5

Objective Residual Effects

| | | |
|---|---|---|
| Attention and Accuracy | Sustained Attention to Response (SART) | No effect (all 4 doses) |
| | Rapid Visual Information Processing | No effect (all 4 doses) |
| | Continuous Tracking Task - deviation | No effect at 8 h (all 4 doses) |
| | Continuous Tracking Task - reaction time | No effect at 10 or 12 h (all 4 doses) |
| Memory | Sternberg Memory Task (STM) | No effect at 8 or 12 h (all 4 doses) |
| | Word Recall - immediate (WRi) | Impaired at 8 h* (2 mg and 2.5 mg doses) |
| | Word Recall - delayed (WRd) | No effect (all 4 doses) |
| Information Processing Sensory Discrimination | Critical Flicker Fusion Test | No effect (all 4 doses) |
| Motor Coordination | Choice Reaction Time - Motor Component | No effect (all 4 doses) |

*immediate word recall was not tested at 10 and 12 hours

When the data was corrected for multiple comparisons, there was no impairment of performance on any of the cognitive or psychomotor tests 8 to 12 hours after the dose was administered. Any residual effects that were observed the morning after dosing were inconsistent. Residual effects did not appear to be dose or time related.

TABLE 6

Subjective Residual Effects at 2.5 mg

| | | |
|---|---|---|
| Subjective assessment (LARS) | Sedation | No impairment |
| | Mood | No impairment |
| | Coordination | No impairment |

Example 2

A single and repeat dose pharmacokinetic safety and pharmacodynamic study of the effects of the compound of formula (II) was conducted using healthy volunteers. The compound of formula (II) in free base form was administered orally in 1 mg, 1.5 mg, 2 mg and 2.5 mg doses via a hard gelatine capsule containing the compound in powder form.

The pharmacokinetic analysis of the results showed that the half-life of the compound of formula (II) is about 3.5 hours. There were no significant differences in the pharmacokinetic profile on day 14 after repeat dosing compared to day 1. Food was found to have little or no effect on the extent of the absorption of the compound of formula (II).

The analysis of the pharmacokinetic data also shows that onset, maintenance and/or terminal insomnia may be treated by administering the compound of formula (II) or a pharmaceutically acceptable salt thereof to achieve an AUC from about 17.5 ng·h/mL to about 600 ng·h/mL, from about 25 ng·h/mL to about 500 ng·h/mL or from about 25 ng·h/mL to about 400 ng·h/mL. For example, the AUC may be from about 52.5 ng·h/mL to about 360 ng·h/mL, from about 75 ng·h/mL to about 300 ng·h/mL, from about 75 ng·h/mL to about 240 ng·h/mL, from about 75 ng·h/mL to about 200 ng·h/mL, from about 75 ng·h/mL to about 150 ng·h/mL, from about 105 ng·h/mL to about 120 ng·h/mL, or any range among all of the above-listed AUC values. Preferably, the AUC is from about 75 ng·h/mL to about 240 ng·h/mL.

The treatment is also conducted to achieve a $C_{max}$ from about 2.5 ng/mL to about 125 ng/mL, from about 7.5 ng/mL to about 75 ng/mL, from about 7.5 ng/mL to about 62.5 ng/mL, from about 7.5 ng/mL to about 37.5 ng/mL, from about 10 ng/mL to about 50 ng/mL, from about 12.5 ng/mL to about 45 ng/mL, from about 15 ng/mL to about 40 ng/mL, or any range among all of the above-listed $C_{max}$ values. Preferably, the $C_{max}$ is from about 15 ng/mL to about 45 ng/mL.

Example 3

A randomized, multicenter, double-blind, placebo-controlled crossover study was conducted to assess the efficacy of the 1.5 mg and 2.5 mg doses of the compound of formula (II) in the treatment of primary insomnia in adult patients. Specifically, one of the objectives of the study was to asses the efficacy of 1.5 mg and 2.5 mg doses on PSG and patient-reported measures of sleep. Also, the study was aimed at assessing the safety of 1.5 mg and 2.5 mg doses.

Figure 5:
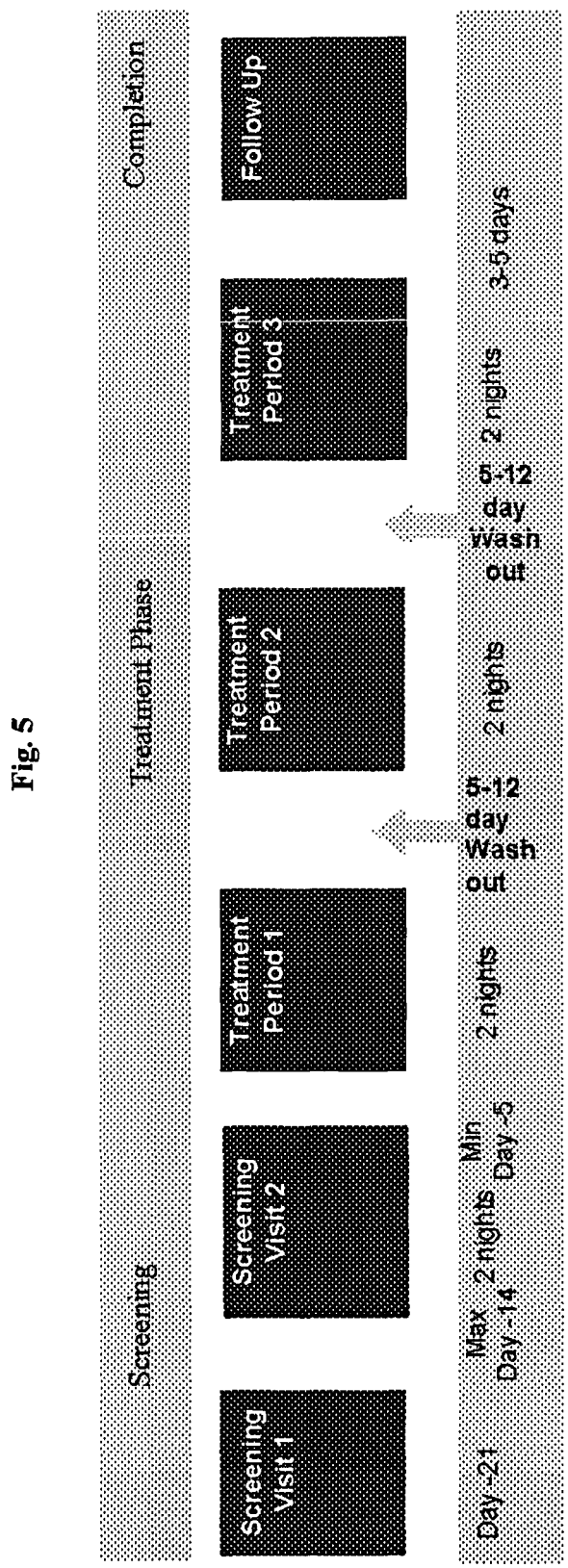
FIG. 5 shows the study design used in Example 3.

The study in this Example was performed for two consecutive nights with a 5-12 day washout between each period. The dosing was conducted 30 minutes before lights were turned out for the night via oral administration of a hard gelatine capsule containing the compound of formula (II) (free base) in powder form. PSG was taken for 8 hours from "lights out" on nights 1 and 2 of each treatment period. Centralized scoring of PSG was used. Testing for residual effects using the Digit Symbol Substitution Test (DSST) was performed at least 30 minutes after wake time (9 hours post dose). The overall study design is shown in FIG. 5.

The study was conducted using 67 subjects younger than 65 years of age (21 males, 46 females; mean age 45.1 yrs, range 23-64 yrs) with a documented diagnosis of primary insomnia (DSM-IV criteria). These subjects' typical bed time was between 9 pm and 1 am with at least 7 hours in bed. These subjects reported sleep latency of at least 45 minutes and TST of not more than 6.5 hours in a sleep diary for at least 3 of 7 nights.

On screening using PSG for 2 nights, the patients showed LPS of more than 20 minutes, with no nights showing LPS of less than 15 minutes. Mean WASO of the patients was at least 40 minutes and mean TST was 240-420 minutes.

The top-line efficacy results of the study in Example 3 are shown in Table 7.

TABLE 7

Top-Line Efficacy Results

| Parameter | 1.5 mg vs. placebo | 2.5 mg vs. placebo |
| --- | --- | --- |
| Adjusted mean TST (min) | p < 0.0001 | p < 0.0001 |
| Adjusted mean WASO (min) | p < 0.0001 | p < 0.0001 |
| Adjusted mean LPS (min) | p < 0.0001 | p < 0.0001 |
| Adjusted mean TWT, $2^{nd}$ half (min) | p = 0.0008 | p < 0.0001 |

Figure 6:
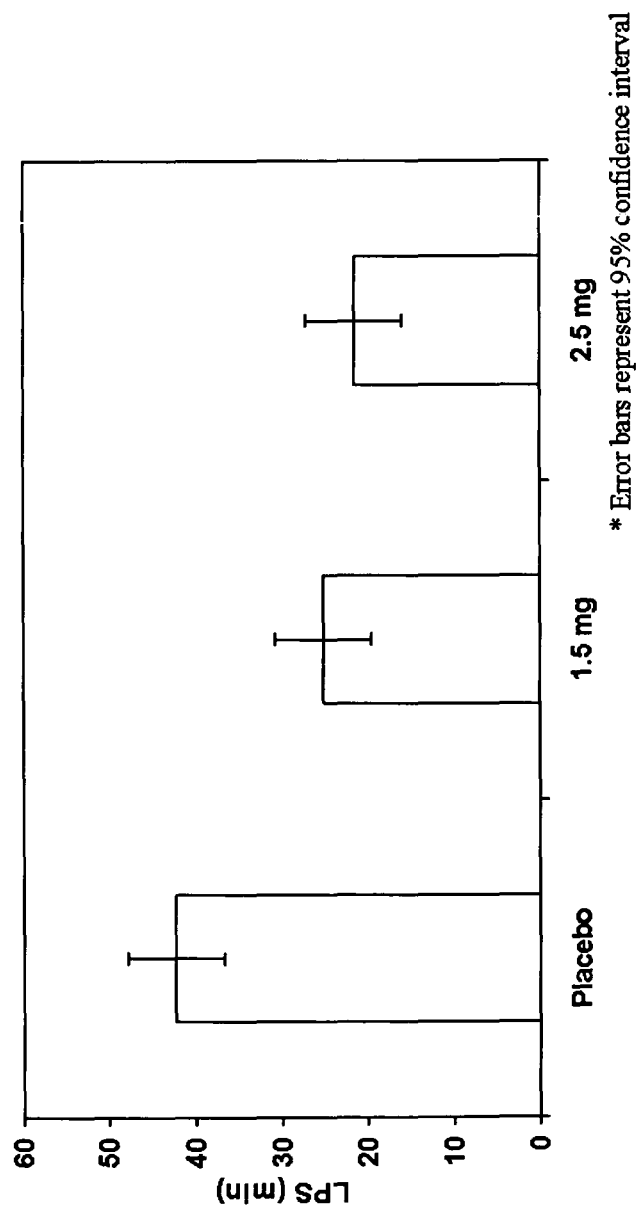
FIG. 6 is a chart showing LPS in Example 3.
Figure 7:
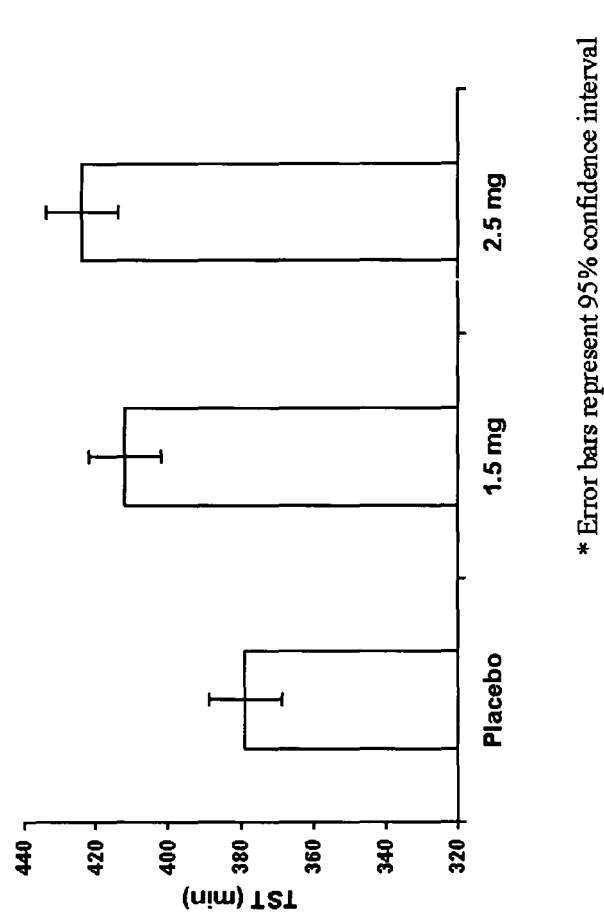
FIG. 7 is a chart showing TST in Example 3.
Figure 8:
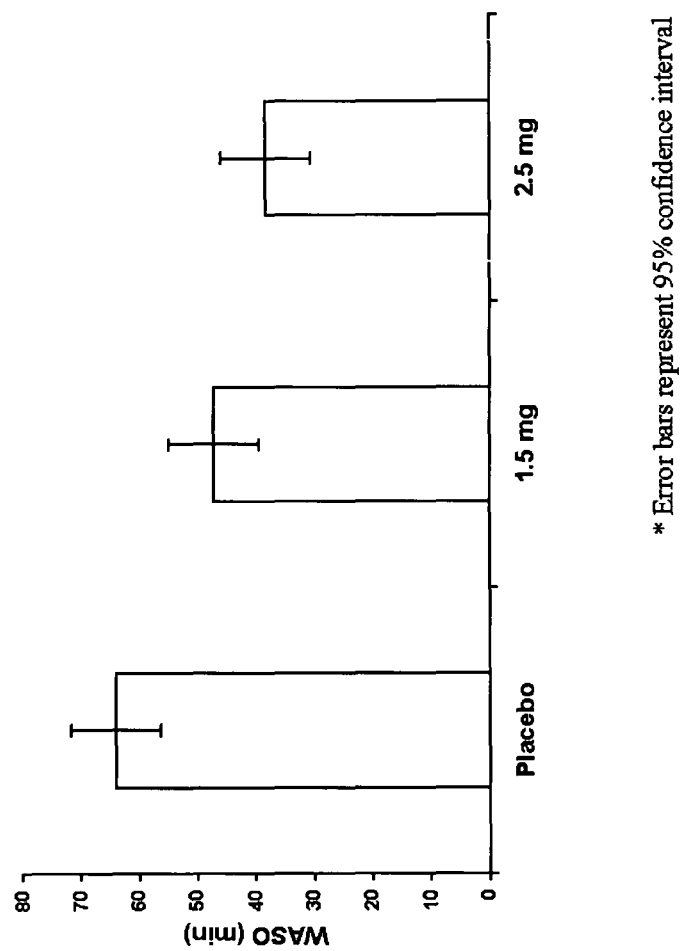
FIG. 8 is a chart showing WASO in Example 3.

The compound of formula (II) showed robust effects on both sleep onset and sleep maintenance. Specifically, compared to a placebo, the 1.5 mg dose reduced LPS by 17.0 minutes (p<0.0001) and the 2.5 mg dose reduced LPS by 20.7 minutes (p<0.0001), as shown in FIG. 6. The 1.5 mg dose increased TST by 33.1 minutes (p<0.0001) and the 2.5 mg dose increased TST by 45.0 minutes (p<0.0001), as shown in FIG. 7, compared to a placebo. The 1.5 mg dose reduced WASO by 16.7 minutes (p<0.0001) and the 2.5 mg dose reduced WASO by 25.7 minutes (p<0.0001), as shown in FIG. 8, compared to a placebo.

Figure 9:
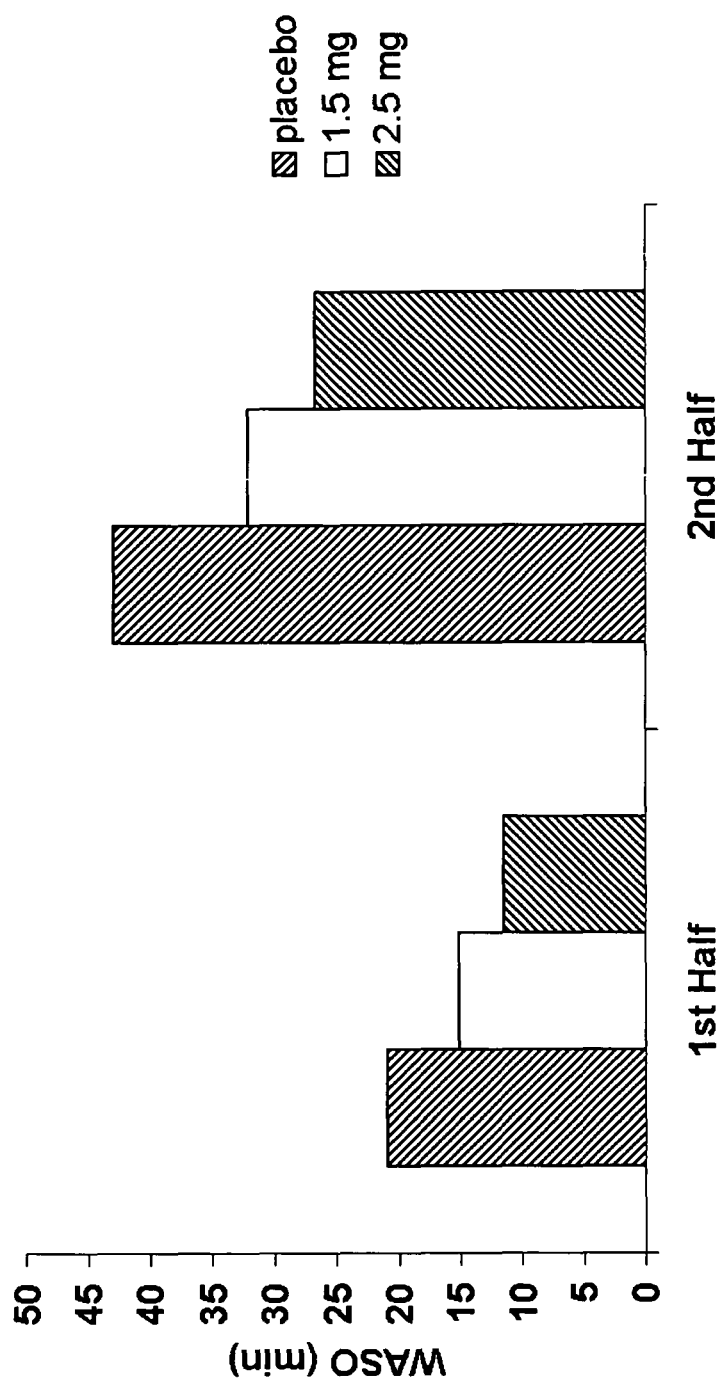
FIG. 9 is a chart showing WASO in the first and second halves of the night in Example 3.
Figure 10:
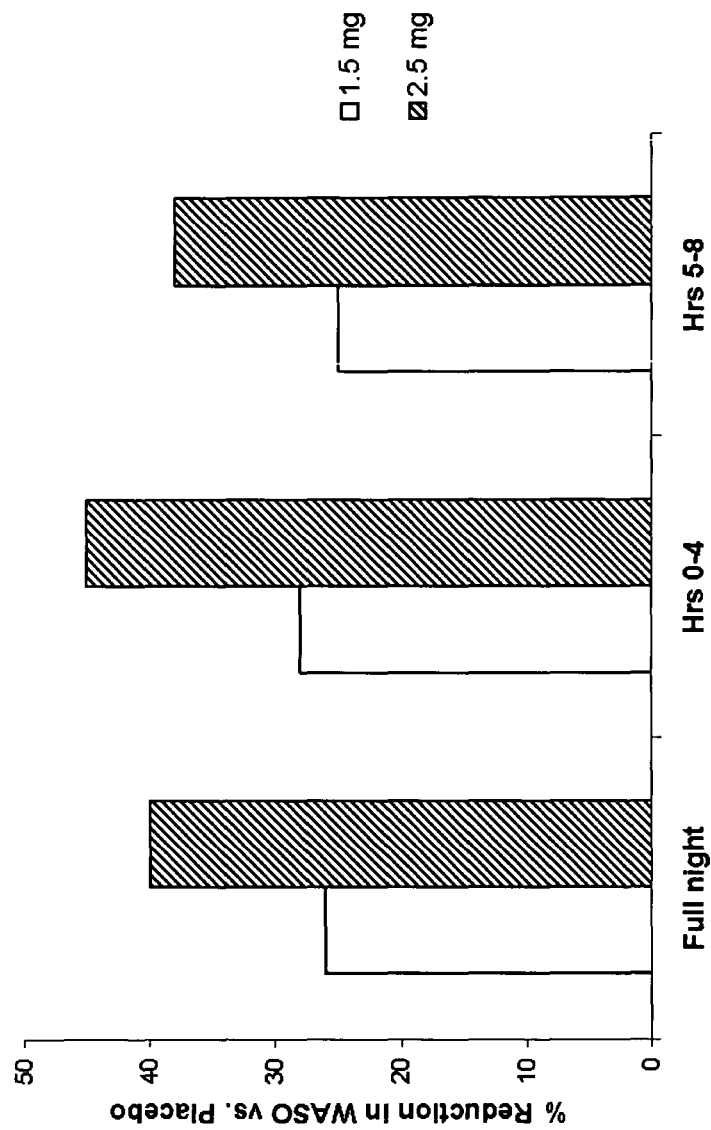
FIG. 10 is a chart showing the percent reduction (vs. placebo) in WASO in Example 3.
Figure 11:
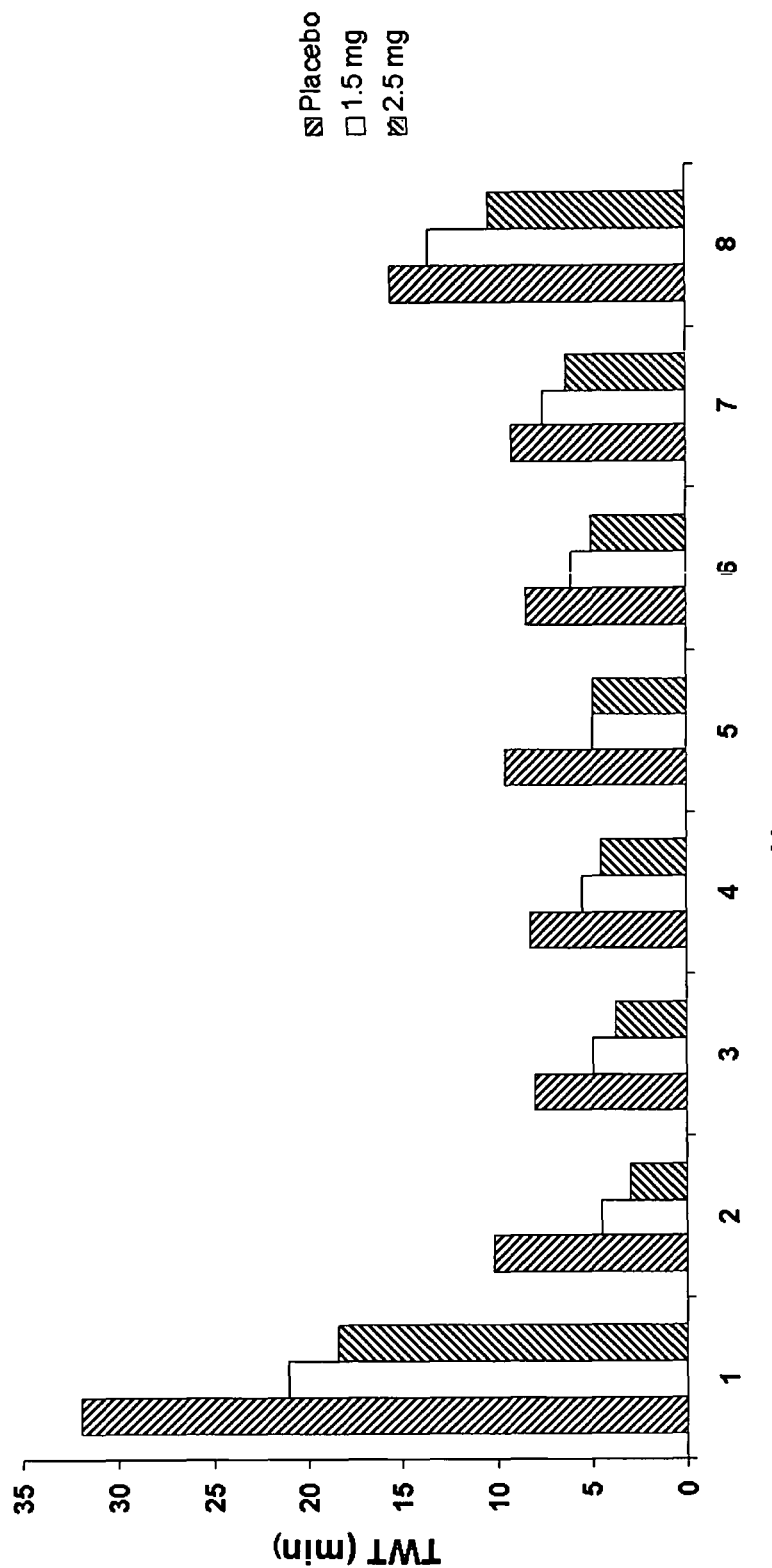
FIG. 11 is a chart showing TWT for each hour of the night in Example 3.

Importantly, as shown in FIGS. 9 and 10 and Table 7, these doses reduced WASO and TWT in the second half of the night (5-8 hours after "lights out") compared to a placebo. Compared to placebo, TWT in hours 5-8 was reduced by 10.8 minutes with the 1.5 mg dose (p=0.0008) and by 16.2 minutes with the 2.5 mg dose (p<0.0001). This demonstrates that the compound of formula (II) can be used to treat terminal insomnia and reduce early morning awakenings. In fact, a reduction in a total amount of time the subject was awake during each hour after dosing was observed, as shown in FIG. 11, with the 2.5 mg dose producing a statistically significant reduction each hour, except hour 7, where p was 0.0577 for the overall treatment effect (reduction in time awake during hour 7 almost reached statistical significance).

These results are particularly unexpected for an agent such as the compound of formula (II). Since it is only a partial agonist at the $GABA_A$ receptor benzodiazepine site and its half-life is similar to some insomnia agents acting as full agonists at this site, which were found ineffective for the treatment of maintenance and terminal insomnia even when used in substantially larger amounts, the compound of formula (II) would be expected to be even less effective than these other agents. It has now been unexpectedly found that this is not the case.

Figure 12:
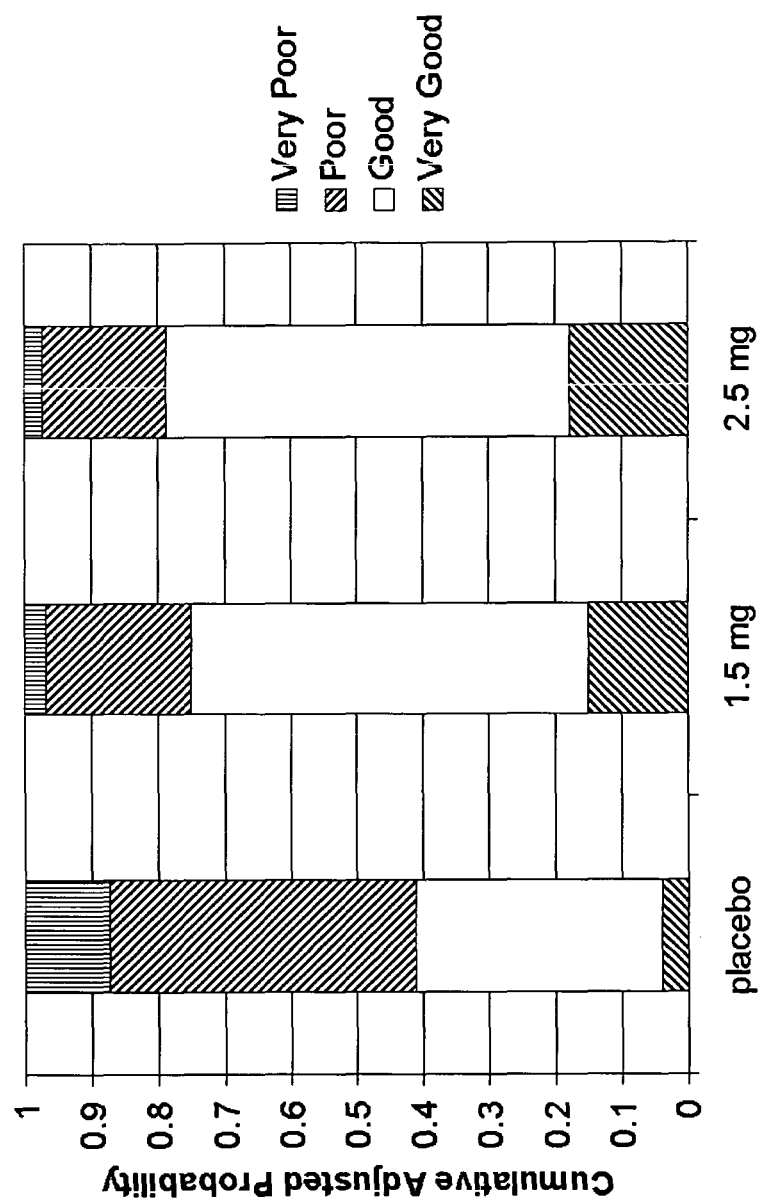
FIGS. 12 and 13 are charts showing patient reported sleep quality in Example 3.
Figure 13:
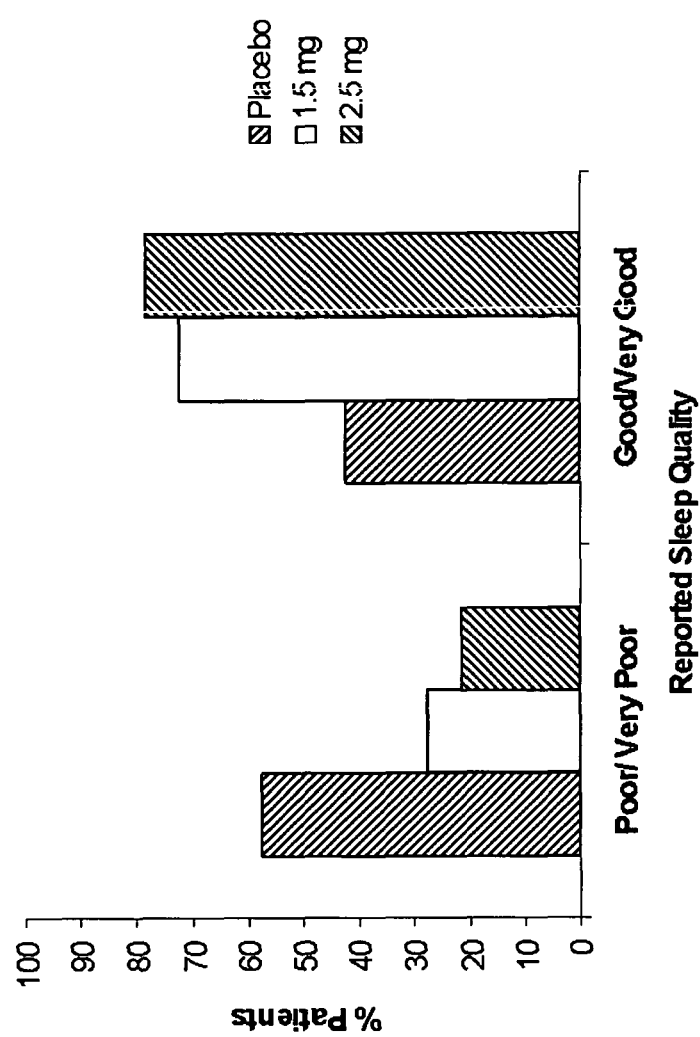
Figure 14:
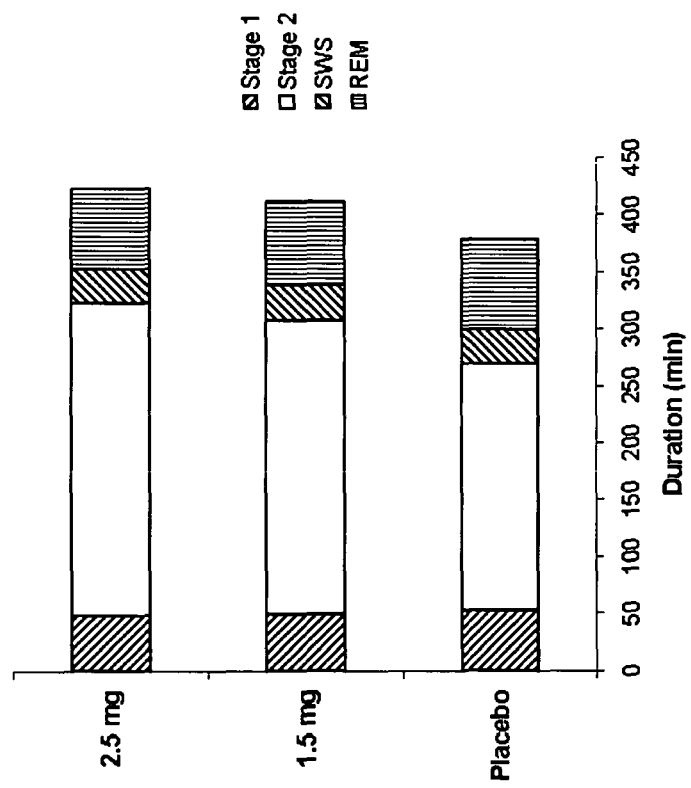
FIG. 14 is a chart showing sleep architecture in accordance with Example 3.

In addition to the improvements in the quantity of sleep, the subjects of the study also reported a marked improvement in sleep quality for both 1.5 and 2.5 mg doses, which is demonstrated in FIGS. 12 and 13. In particular, the compound of formula (II) was found to produce sleep architecture, which is equivalent to the natural sleep architecture (i.e., when no medicaments are administered). There was no impairment of slow wave sleep, and only a small effect on REM sleep was observed. These results are demonstrated by the chart in FIG. 14.

Maintaining normal sleep architecture is a very important component of getting a good night rest. Some conventional insomnia medications, such as classic benzodiazepines, may have the ability to induce and maintain sleep, but they do so by considerably altering the normal sleep architecture, which results in unrefreshing sleep and other side effects.

Figure 15:
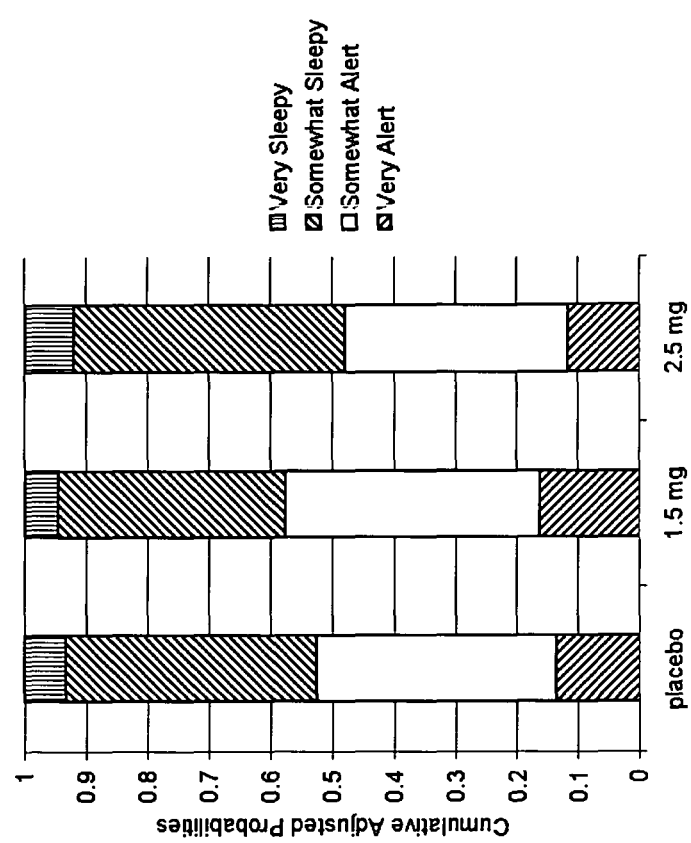
FIG. 15 is a chart showing patient reported residual sedation effects in accordance with Example 3.

The results of the study conducted in accordance with Example 3 showed that the compound of formula (II) produces no patient-reported residual sedation effects at either the 1.5 mg dose or the 2.5 mg dose compared with the placebo. This is demonstrated by the chart in FIG. 15.

The objective residual effects of the administration of the compound of formula (II) were also evaluated. The scores on the DSST taken by the subjects 9 hours after administering the dose were only slightly lower than those obtained from the subjects who were administered the placebo.

The results also showed that the compound of formula (II) was safe and well-tolerated at 1.5 mg and 2.5 mg doses. No serious side effects, and only a low incidence of adverse events, were reported. These results are summarized in Table 8.

TABLE 8

Safety Results

| Adverse Event | Placebo (n* = 70) | 1.5 mg (n* = 71) | 2.5 mg (n* = 71) |
| --- | --- | --- | --- |
| Number of Patients with Any Event[†] | 12 (17.1%) | 13 (18.3%) | 18 (25.4%) |
| Number of Patients with Headache | 3 (4.3%) | 3 (4.2%) | 6 (8.5%) |
| Number of Patients with Somnolence | 0 (0%) | 2 (2.8%) | 4 (5.6%) |

*"n" refers to the total number of patients enrolled in the study
[†]reported at any time in the study irrespective of whether these events were considered related to the medication Example 4

A randomized, double-blind, placebo-controlled parallel group design was used to assess the hypnotic efficacy of 1.5 mg and 2.5 mg doses of the compound of formula (II) following 7 nights dosing using 149 subjects. The study was conducted in 20 sleep laboratories in the United States using both objective and subjective measures. PSG data was collected on nights 1, 6 and 7 and results are based on the mean data from these three nights. The compound of formula (II) was administered in free base form as a powder in a capsule. The details of the study design are shown in FIG. 17.

The subjects were males and females at least 65 years old with a documented diagnosis of primary insomnia (DSM-IV criteria). These subjects' typical bed time was between 9 pm and 1 am with at least 7 hours in bed. These subjects reported five nights or more in seven days with TST of not more than 6.5 hours with at least 7 hours in bed. The subjects had a history of sleepiness, tiredness, or unintentional napping during the daytime, which the subjects attribute to poor sleep at night. On screening using PSG for 2 nights, mean TST was 240-420 minutes. Mean latency in Multiple Sleep Latency Test (MSLT) was at least 5.5 minutes and not more than 14 minutes.

PSG was used to obtain TST (average of nights 1, 6 and 7). The daytime function (day 8) was measured using Psychomotor Vigilance Task (PVT), MSLT (MSLT Clinical Guidelines; Sleep, 1(3): 260-276 (1992)), Karolinska Sleepiness Scale (KSS); and objective measures Rey Auditory Verbal Learning Test (RAVLT) (day 8) (assessed 30±10 minutes after lights-on). Sleep architecture, subject reported sleep variables and categorical rating of sleep quality and safety endpoints including the Benzodiazepine Withdrawal Questionnaire were also determined.

This study showed a highly significant improvement between both doses of the compound of formula (II) and placebo in the primary endpoint of PSG-derived TST. Compared to placebo, mean TST increased by 30.9 minutes (9%) at 1.5 mg and 56.4 minutes (17%) at 2.5 mg (p=0.0001 and p=<0.0001 respectively).

Significant improvements were also seen across key PSG-derived secondary endpoints, including WASO and LPS. The 2.5 mg dose also showed a significant effect on WASO during the second half of the night, indicating that compound of formula (II) is highly effective in maintaining sleep throughout the night. This was further confirmed by the hour-by-hour analysis of TWT. Treatment with compound of formula (II) produced a statistically significant reduction in TWT for all hours of the night apart from hour 7.

Table 9 below shows the results for the primary and key secondary PSG endpoints (average of nights 1, 6 and 7).

TABLE 9

Primary And Key Secondary PSG Endpoints

| Parameter<br>n = 149 | Placebo | 1.5 mg | 2.5 mg |
|---|---|---|---|
| Adjusted mean TST (min)/% change from placebo | 338.6 | 369.5/9%<br>p = 0.0001 | 395/17%<br>p = <0.0001 |
| Adjusted mean WASO (min)/% change from placebo | 101.4 | 86.2/15%<br>p = 0.0140 | 65.3/36%<br>p = <0.0001 |
| Adjusted mean LPS (min)/% change from placebo | 46.5 | 30.5/34%<br>p = 0.0091 | 26.5/43%<br>p = 0.0014 |

"n"—number of subjects that were randomized into the study

Table 10 shows non-PSG efficacy measures. These results were supported by subject-reported measures including sTST, sSOL (subjective sleep onset latency) and sWASO.

TABLE 10

Non-PSG Efficacy Measures

| Parameter | 1.5 mg vs. placebo | 2.5 mg vs. placebo |
|---|---|---|
| MSLT | p = 0.0257 | p = 0.0295 |
| Subject reported sleep quality (Night 1) | p < 0.0001 | p < 0.0001 |
| sTST | p = 0.0015 | p < 0.0001 |
| sWASO | p = 0.0110 | p = 0.0005 |
| sSOL | p = 0.0062 | p = 0.0003 |

Overall, the results showed no significant differences between placebo and either dose of the compound of formula (II) in the PVT or RAVLT. Also, overall, no significant difference was seen subjectively in the KSS. No significant difference was seen in the Benzodiazepine Withdrawal Questionnaire.

The specific results are shown in FIGS. 18-29 and discussed below.

Figure 18:
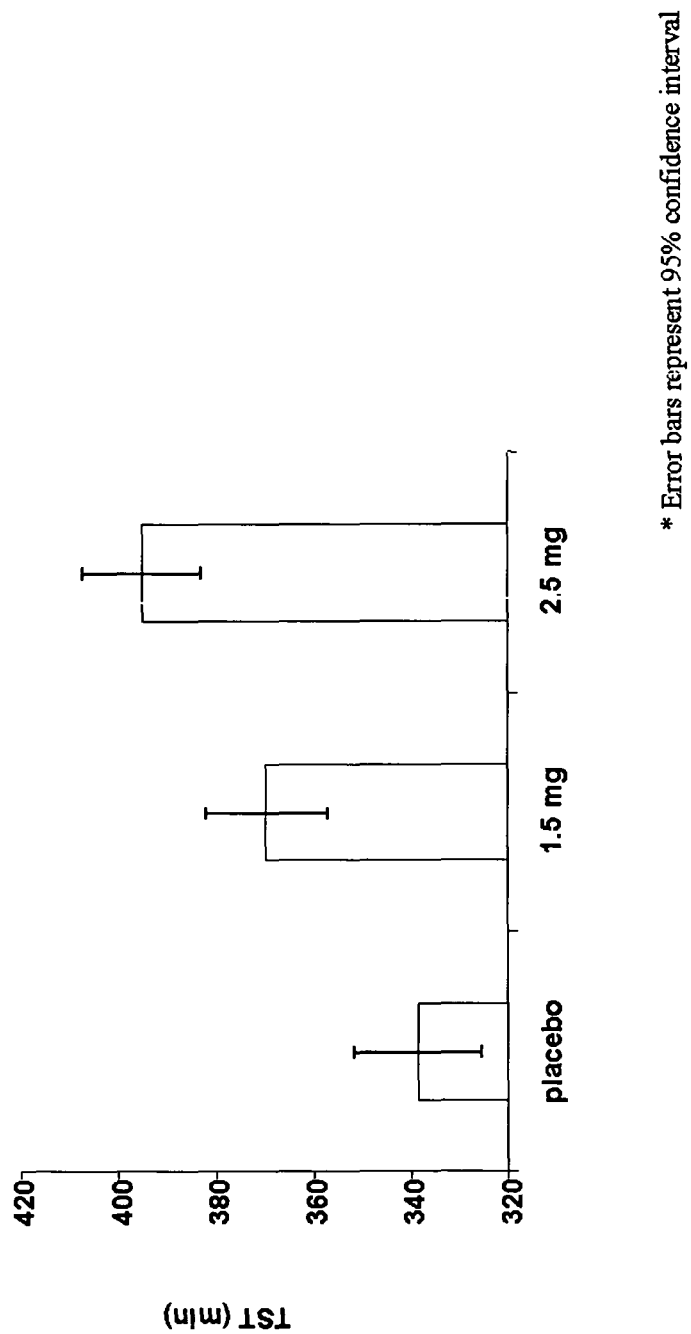
FIG. 18 is a chart showing PSG-derived TST (average of nights 1, 6 & 7) in Example 4.
Figure 19:
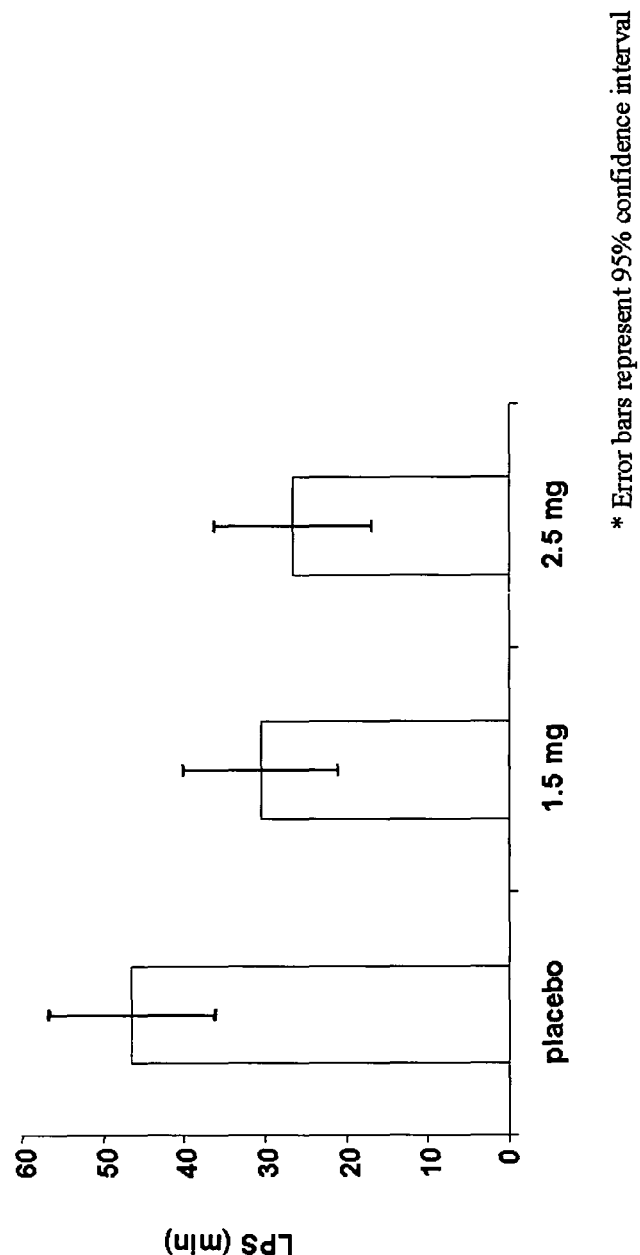
FIG. 19 is a chart showing PSG-derived LPS in Example 4.
Figure 20:
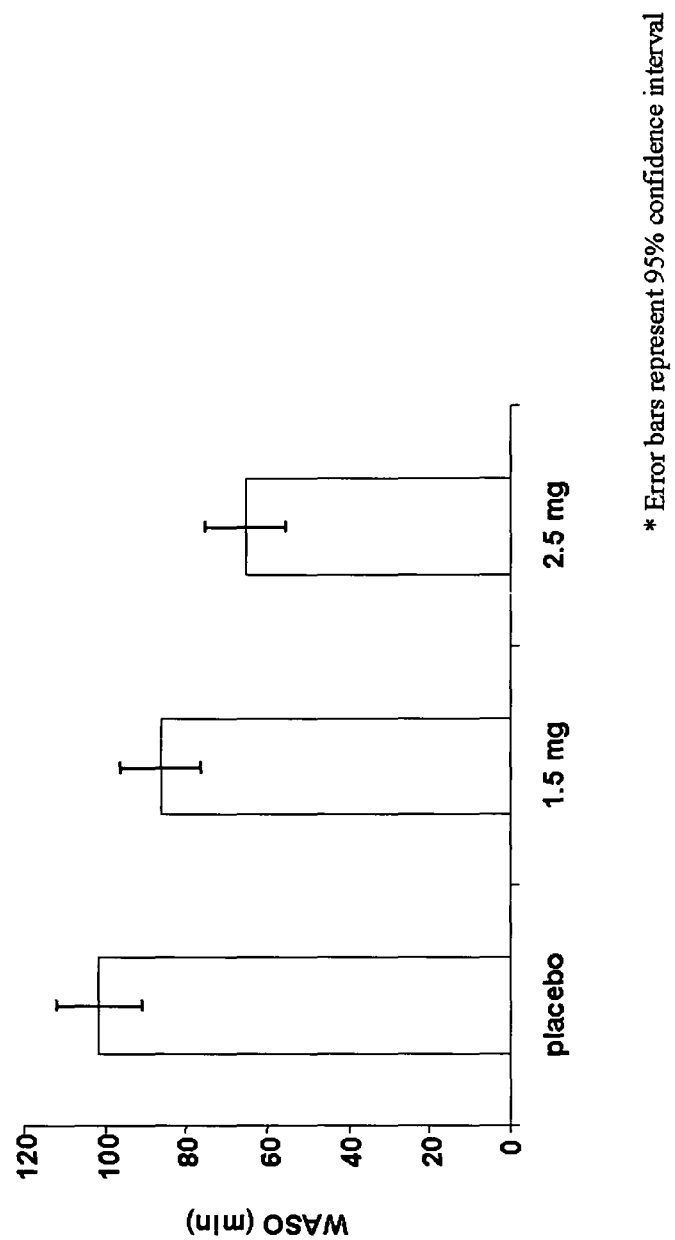
FIG. 20 is a chart showing WASO (over the whole night, i.e., 8 hours) in Example 4.
Figure 21:
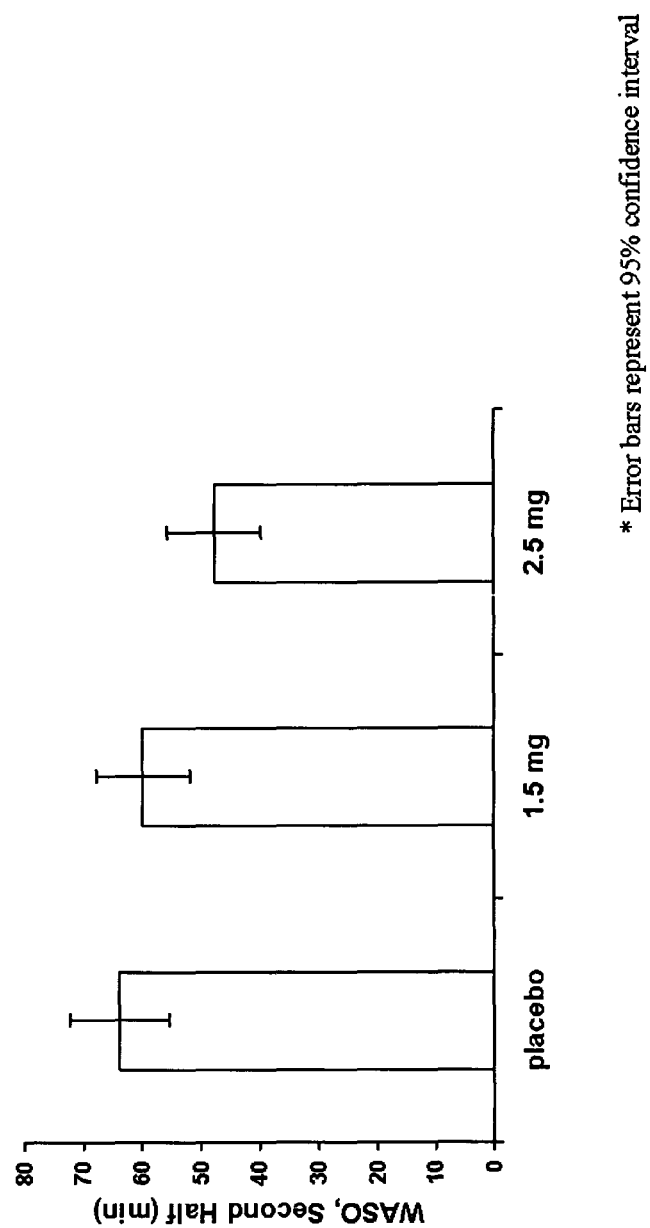
FIG. 21 is a chart showing WASO in the second half of the night (5-8 hours after "lights out") in Example 4.
Figure 22:
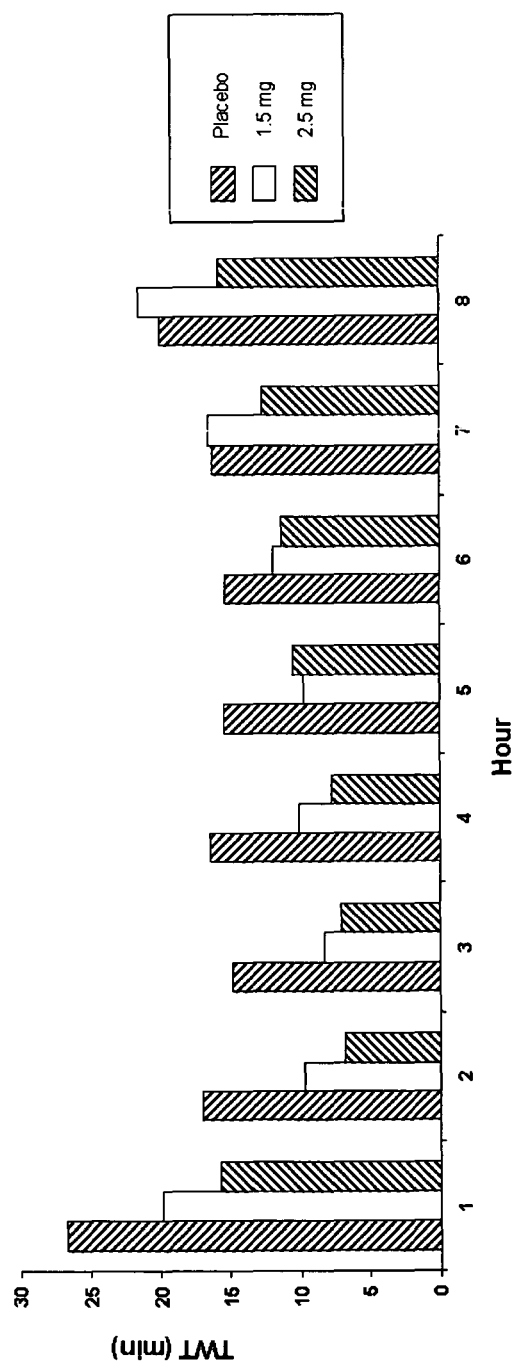
FIG. 22 is a chart showing TWT hour by hour in Example 4.

FIG. 18 shows that both 1.5 mg and 2.5 mg doses increased total sleep time in the elderly compared to the placebo. FIG. 19 shows that the 1.5 mg dose decreased LPS by 34% and the 2.5 mg dose decreased LPS by 43% compared to the placebo. FIG. 20 shows that the 1.5 mg dose decreased WASO by 15% and the 2.5 mg dose decrease WASO by 36% compared to the placebo. FIG. 21 shows that there was a significant decrease in WASO in the second half of the night (5-8 hours after "lights out") when the dose was 2.5 mg. FIG. 22 shows that the 2.5 mg dose significantly reduced TWT every hour, except hour 7, where the overall treatment effect was not statistically significant. The 1.5 mg dose significantly reduced total wake time each hour up to hour 6.

Figure 23:
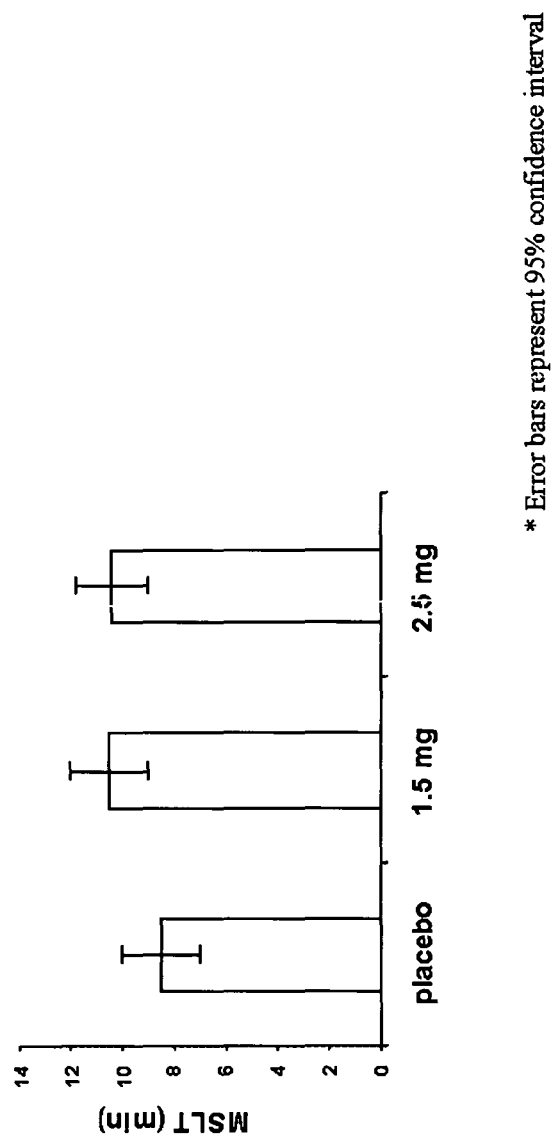
FIG. 23 is a chart showing average sleep latency over all timepoints tested (2, 4, 6, 8 & 10 hours post wake time) in Example 4 using the Multiple Sleep Latency Test (MSLT).

Daytime function (daytime sleepiness) was measured using the MSLT, as shown in FIG. 23. The average sleep latency over all timepoints tested (2, 4, 6, 8 & 10 hours post wake time) was increased, demonstrating that the compound of formula (II) improves daytime function by reducing daytime sleepiness.

Figure 24:
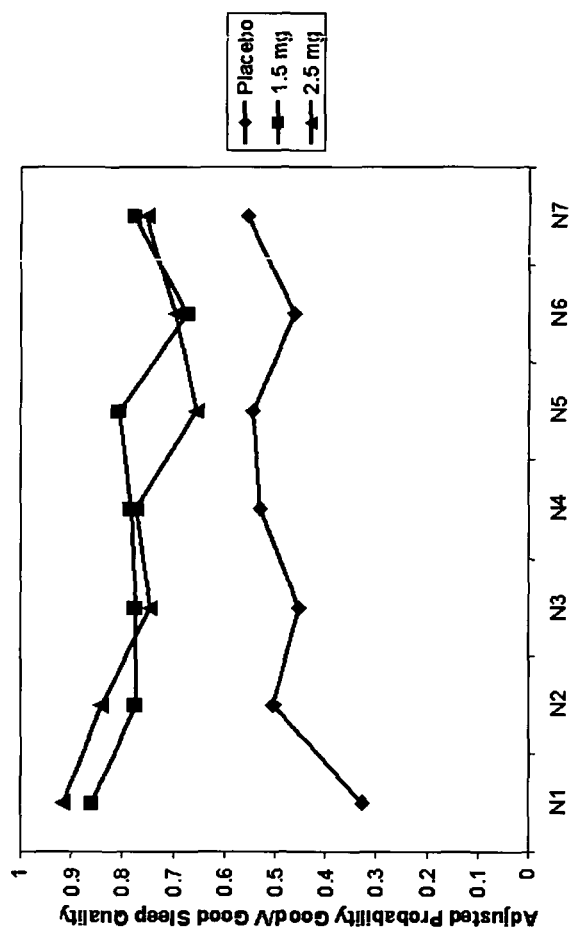
FIG. 24 is a chart showing subjective sleep quality based on the adjusted probability of good/very good sleep quality in Example 4.
Figure 25:
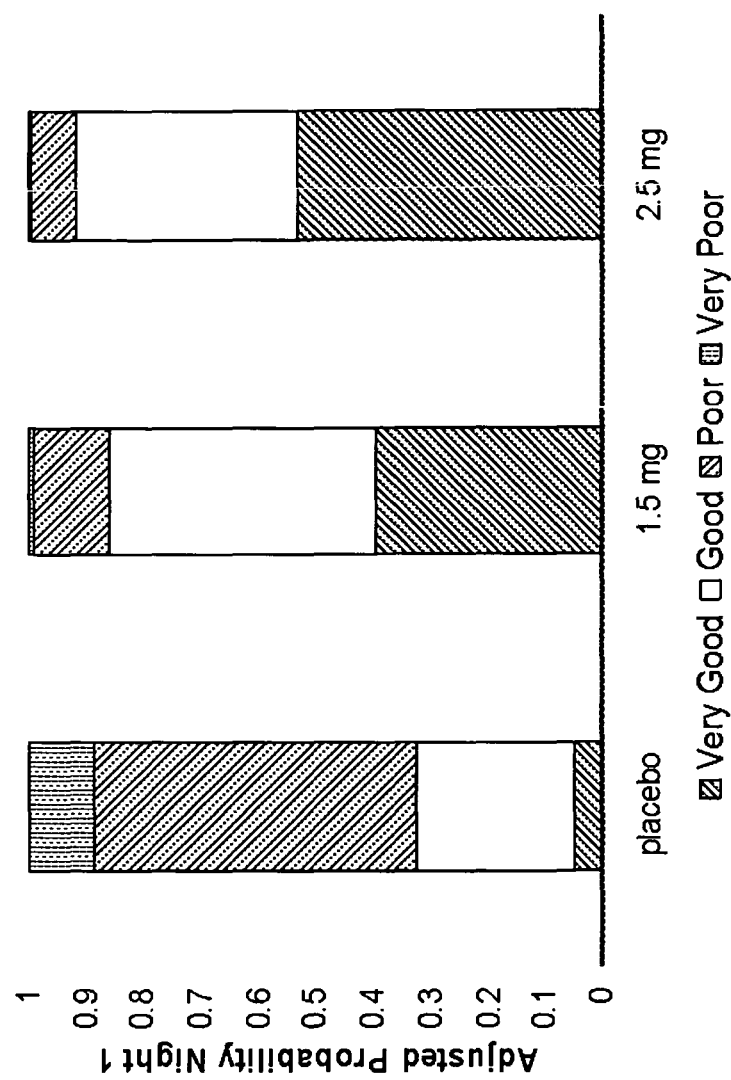
FIG. 25 shows subject-reported sleep quality during night 1 in accordance with the study in Example 4.

As demonstrated by the chart in FIG. 24, subjective sleep quality showed sustained improvement over all 7 nights of dosing. Subject-reported sleep quality during night 1 is shown in FIG. 25, where both doses markedly improved categorical ratings of sleep quality (p<0.0001) on night 1.

Figure 26:
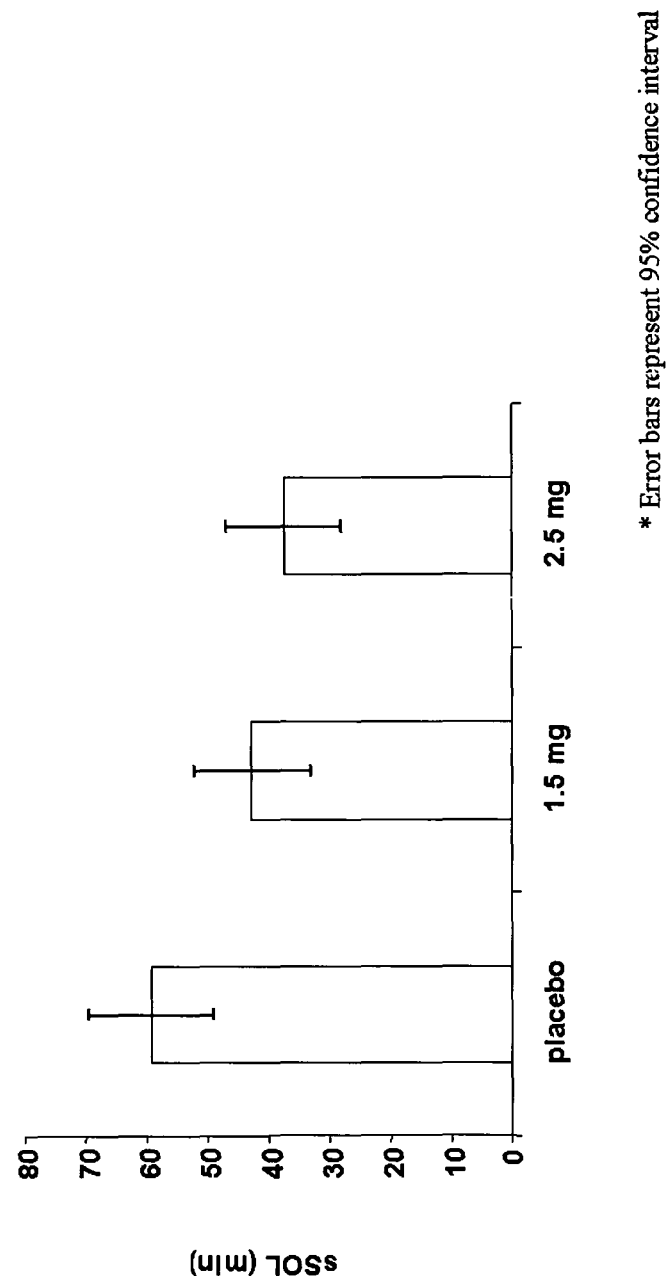
FIG. 26 is a chart showing subjective (subject-reported) sleep onset latency (adjusted mean sleep onset latency across all 7 nights) in Example 4.
Figure 27:
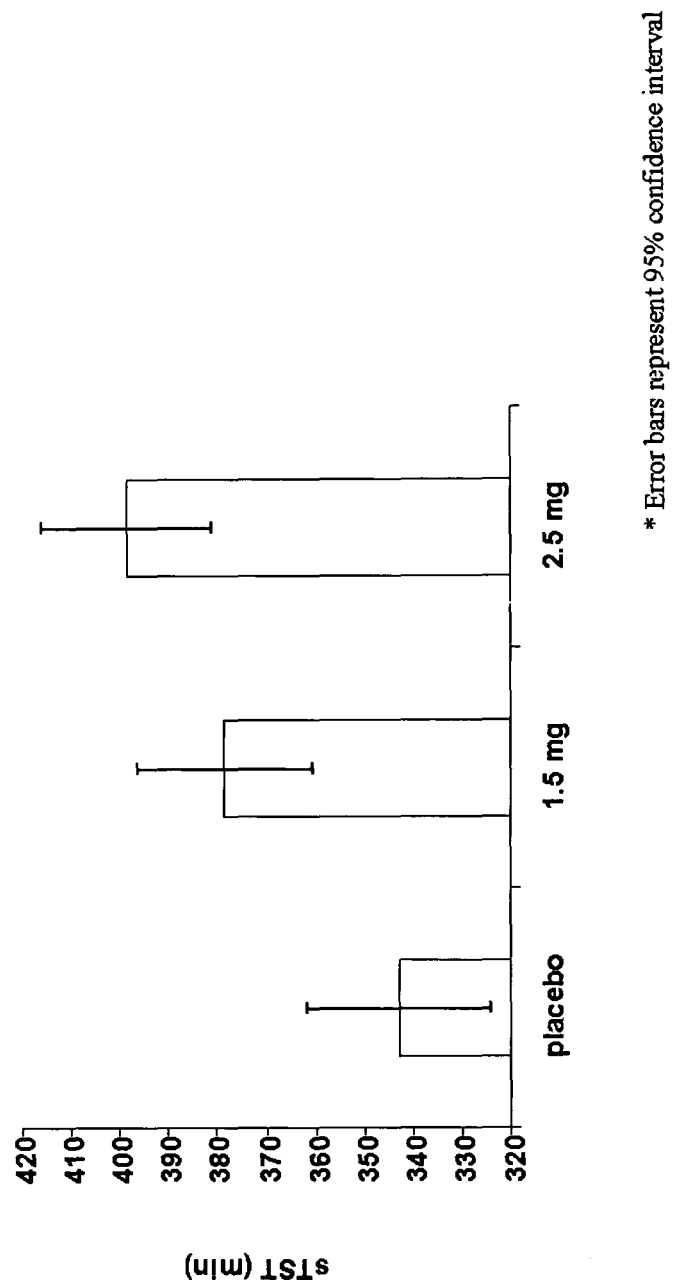
FIG. 27 is a chart showing subjective (subject-reported) TST (adjusted mean sTST across all 7 nights) in Example 4.
Figure 28:
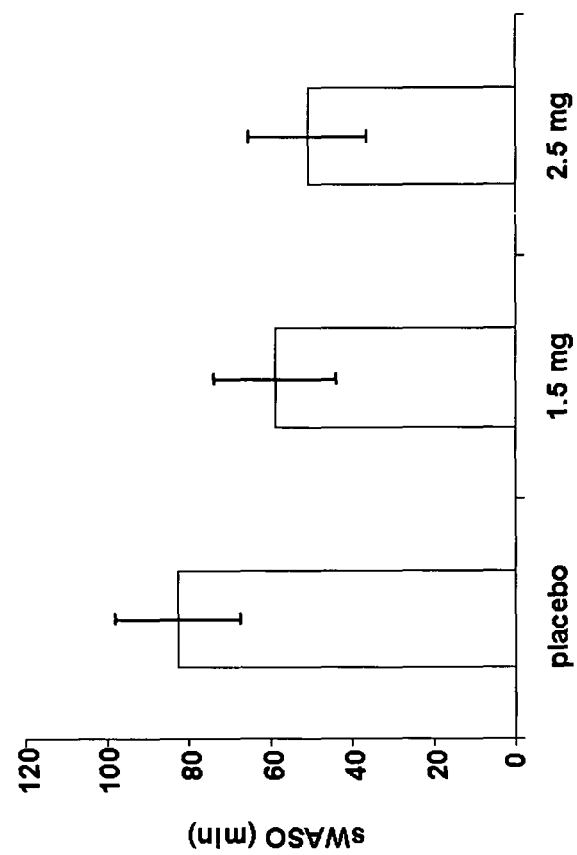
FIG. 28 is a chart showing subjective (subject-reported) WASO (sWASO) (mean sWASO across all 7 nights dosing) in Example 4.

The subjects spent nights 1, 6 and 7 in the sleep laboratory and were at home on nights 2-5. They were asked to rate their sleep quality as very poor, poor, good or very good. FIG. 26 shows that both the 1.5 mg dose and the 2.5 mg dose produced a significant reduction in subject-reported sleep onset latency. FIG. 27 shows that both of these doses also produced a significant increase in sTST, and FIG. 28 shows that these doses produced a significant decrease in sWASO.

Figure 29:
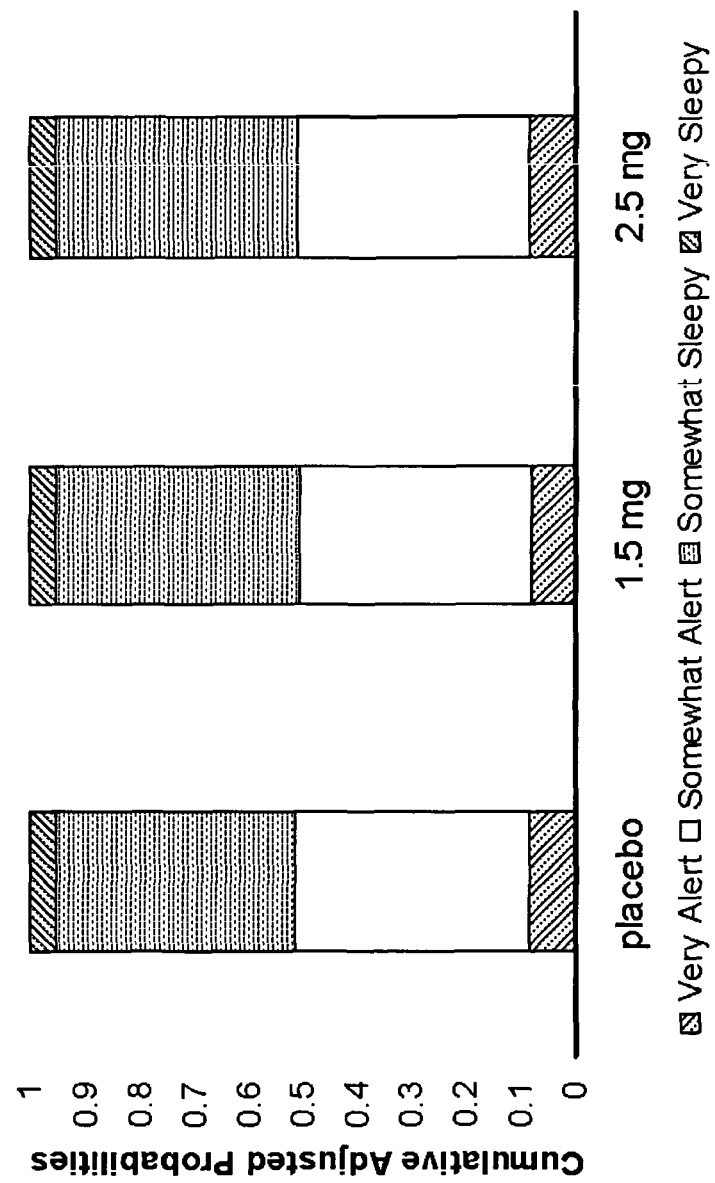
FIG. 29 shows cumulative adjusted probabilities for patient-reported residual effects in Example 4.

The subjects were also asked to report their residual sedation. As can be seen in FIG. 29, neither the administration of the 1.5 mg dose or the 2.5 mg dose produced residual sedation effects, since the results are comparable to those of a placebo.

The results also showed that the compound of formula (II) was safe and well-tolerated at 1.5 mg and 2.5 mg doses. No serious treatment emergent adverse events were reported during the study. The majority of adverse events reported were mild and infrequent. The most common adverse events were dizziness, headache and somnolence and the percentage of patients reporting these events is shown in the table below. These results are summarized in Table 11.

TABLE 11

Safety Results

|  | Placebo<br>(n = 44) | 1.5 mg<br>(n = 53) | 2.5 mg<br>(n = 52) |
|---|---|---|---|
| Number of subjects with any event (%)[†] | 7 (15.9) | 15 (28.3) | 19 (36.5) |
| Dizziness | 0 (0) | 3 (5.7) | 5 (9.6) |
| Headache | 0 (0) | 5 (9.4) | 3 (5.8) |
| Somnolence | 1 (2.3) | 1 (1.9) | 6 (11.5) |

"n"—number of subjects that were randomized into the study
[†]reported at any time in the study irrespective of whether these events were considered related to the medication Overall, the study in this Example showed that the compound of formula (II) has robust effects on both sleep onset and sleep maintenance. The PSG analysis showed that the compound of formula (II) generally preserved sleep architecture. These PSG results were supported by subject-reported measures, including sTST, sSOL and sWASO. Subjectively, sleep quality was improved on all nights and there was no residual sedation assessed 30-minutes post wake time (approximately 9 hours post dose).

An additional element of the study design was to assess daytime function on Day 8. This included the MSLT, which is an objective assessment of daytime sleepiness. Initial analyses showed that both doses of the compound of formula (II) produced a statistically significant overall improvement in the MSLT across the day compared to placebo indicating that the subjects were more alert following treatment with the compound of formula (II). This is particularly surprising since many conventional insomnia agents not only fail to improve daytime activity in the elderly, but some, particularly those with longer half-lives, exacerbate the already existing daytime sleepiness.

Daytime function was further assessed objectively using the RAVLT and PVT and subjectively using the KSS. Initial analyses suggest overall that there was no significant difference between the compound of formula (II) and placebo.

No significant difference was seen between either dose of the compound of formula (II) and placebo in the Benzodiazepine Withdrawal Questionnaire.

The results in Example 4 demonstrate the effects of the compound of formula (II) on sleep onset and sleep maintenance in the elderly population and indicate that the 1.5 mg and 2.5 mg doses have hypnotic efficacy in the elderly with no significant residual effects.

While the invention has been described in conjunction with the detailed description thereof and the accompanying figures, the foregoing description is intended to illustrate and not limit the scope of the invention, which is defined by the scope of the appended claims. Other aspects, advantages, and modifications are within the scope of the following claims.

What is claimed is:

1. A method for treating maintenance insomnia in a human in need thereof comprising administering to the human before bedtime an amount of a compound of formula (II) or a pharmaceutically acceptable salt thereof effective to treat the maintenance insomnia and to increase total sleep time in a period of about four to about eight hours after administration

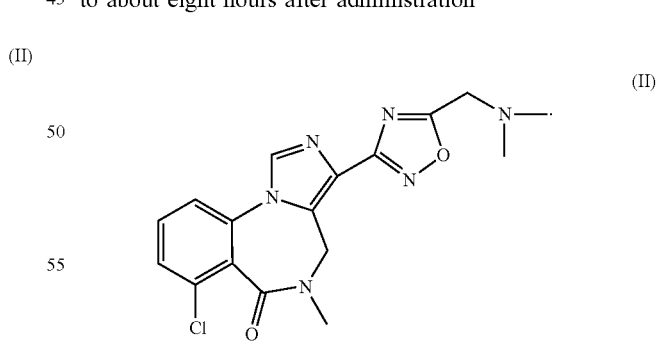

2. The method according to claim 1, wherein the amount of the compound of formula (II) or the pharmaceutically acceptable salt thereof is from about 0.5 mg to about 5 mg.

3. The method according to claim 1, wherein the amount of the compound of formula (II) or the pharmaceutically acceptable salt thereof is from about 1 mg to about 3 mg.

4. The method according to claim 1, wherein the amount of the compound of formula (II) or the pharmaceutically acceptable salt thereof is from about 1.5 mg to about 2.5 mg.

5. The method according to claim 1, wherein the human is at least 65 years old.

6. A method for treating terminal insomnia in a human in need thereof comprising administering to the human before bedtime an amount of a compound of formula (II) or a pharmaceutically acceptable salt thereof effective to treat the terminal insomnia and to increase total sleep time in a period of about four to about eight hours after administration

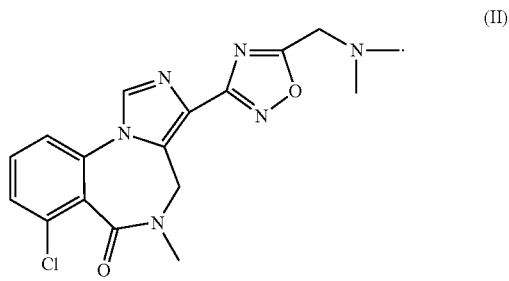 [SMILES: CN(C)Cc1nc(-c2ncn3c2CN(C)C(=O)c2c(Cl)cccc2-3)no1]

7. The method according to claim 6, wherein the amount of the compound of formula (II) or the pharmaceutically acceptable salt thereof is from about 0.5 mg to about 5 mg.

8. The method according to claim 6, wherein the amount of the compound of formula (II) or the pharmaceutically acceptable salt thereof is from about 1 mg to about 3 mg.

9. The method according to claim 6, wherein the amount of the compound of formula (II) or the pharmaceutically acceptable salt thereof is from about 1.5 mg to about 2.5 mg.

10. The method according to claim 6, wherein the human is at least 65 years old.

11. The method according to claim 6, which is also for treatment of maintenance insomnia, wherein the compound of formula (II) or the pharmaceutically acceptable salt thereof is administered to the human in need of treatment of the maintenance insomnia and the terminal insomnia.

12. A method for increasing total sleep time in a period in a human in need thereof comprising administering to the human before bedtime an amount of a compound of formula (II) or a pharmaceutically acceptable salt thereof effective to increase total sleep time in the period, which is about four to about eight hours after administration

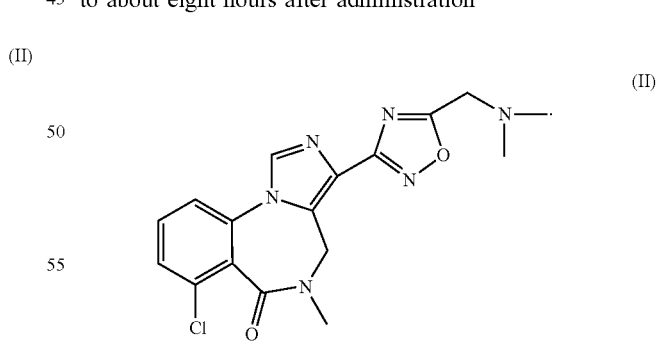

13. The method according to claim 12, wherein the amount of the compound of formula (II) or the pharmaceutically acceptable salt thereof is from about 0.5 mg to about 5 mg.

14. The method according to claim 12, wherein the amount of the compound of formula (II) or the pharmaceutically acceptable salt thereof is from about 1 mg to about 3 mg.

15. The method according to claim 12, wherein the amount of the compound of formula (II) or the pharmaceutically acceptable salt thereof is from about 1.5 mg to about 2.5 mg.

16. The method according to claim 12, wherein the human is at least 65 years old.

17. The method according to claim 12, wherein the period is from about five to about eight hours after administration.

18. The method according to claim 12, wherein the period is from about six to about eight hours after administration.

* * * * *